United States Patent
Tran et al.

(10) Patent No.: US 11,517,458 B2
(45) Date of Patent: Dec. 6, 2022

(54) IMPLANT DELIVERY SYSTEM

(71) Applicant: MicroVention, Inc., Aliso Viejo, CA (US)

(72) Inventors: Vivian Tran, San Juan Capistrano, CA (US); Kaushik Joshi, Tustin, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 441 days.

(21) Appl. No.: 16/376,958

(22) Filed: Apr. 5, 2019

(65) Prior Publication Data

US 2019/0307588 A1 Oct. 10, 2019

Related U.S. Application Data

(60) Provisional application No. 62/653,429, filed on Apr. 5, 2018.

(51) Int. Cl.
*A61F 2/966* (2013.01)
*A61F 2/95* (2013.01)

(52) U.S. Cl.
CPC ............ *A61F 2/966* (2013.01); *A61F 2/9517* (2020.05)

(58) Field of Classification Search
CPC . A61F 2/95–2/97; A61F 2/2427; A61F 2/243; A61F 2/2433; A61F 2/2436; A61F 2/2439
See application file for complete search history.

(56) References Cited

U.S. PATENT DOCUMENTS

| | | | |
|---|---|---|---|
| 2004/0006380 A1* | 1/2004 | Buck | A61F 2/966 623/1.11 |
| 2004/0093061 A1* | 5/2004 | Acosta | A61F 2/915 623/1.11 |
| 2005/0256562 A1* | 11/2005 | Clerc | A61F 2/95 623/1.11 |
| 2010/0094310 A1* | 4/2010 | Warring | A61M 25/0606 606/108 |
| 2010/0191326 A1* | 7/2010 | Alkhatib | A61F 2/013 623/2.11 |
| 2014/0135909 A1* | 5/2014 | Carr | A61F 2/2436 623/2.11 |
| 2014/0288630 A1* | 9/2014 | Gerdts | A61F 2/966 623/1.12 |
| 2017/0079820 A1* | 3/2017 | Lam | A61F 2/82 |
| 2018/0071094 A1* | 3/2018 | Alon | A61F 2/0077 |

* cited by examiner

*Primary Examiner* — Kathleen S Holwerda
(74) *Attorney, Agent, or Firm* — Inskeep IP Group, Inc.

(57) ABSTRACT

A delivery system used for vascular implant delivery is described. In some embodiments, the delivery system includes a user-gripped handle used to aid in retracting and advancing an implant. In some embodiments, the delivery system includes a telescoping pusher system to aid in retracting and advancing an implant.

17 Claims, 20 Drawing Sheets

IMPLANT DELIVERY SYSTEM

RELATED APPLICATIONS

This application claims priority to U.S. Provisional Application Ser. No. 62/653,429 filed Apr. 5, 2018 entitled Implant Delivery, which is hereby incorporated herein by reference in its entirety.

BACKGROUND OF THE INVENTION

Implants, such as stents, typically utilize an elongated pusher used to track the implant through an overlying delivery catheter. These pushers must be relatively long to properly track through the length of an entire delivery catheter. However, this length can introduce complications during the manufacturing process and may also present difficulty in avoiding damage to the devices when shipping. Hence, there is a need for an implant delivery system that can utilize a shorter or easier delivery profile.

Typical pushing systems rely on the user to physically push/pull the device to properly place the implant which can make precise placement of the implant difficult given the relatively small dimensions of the human vasculature, particularly in the smaller blood vessels (e.g., in the neurovasculature). Hence, there is also a need for an implant delivery system that would allow for precise placement for implant delivery.

SUMMARY OF THE INVENTION

The present invention relates to an implant delivery system used to deliver a vascular implant, such as a vascular prosthesis, such as a stent or stent-graft. In some embodiments, a telescoping pusher system is utilized where an inner pusher element and outer pusher element are utilized. In one embodiment, an inner solid or tubular element is located within an outer tubular sleeve, and this inner element is distally connected to the implant.

In one embodiment, a pusher and pusher system include an inner element and an outer tubular sleeve. The inner element includes a protruding flange and the outer sleeve includes an inner stopper which limits the displacement of the inner element relative to the outer sleeve.

In one embodiment, a pusher and pusher system include an inner element and an outer tubular sleeve. The inner element includes a protruding pin and the outer sleeve includes a recess sized to fit the protruding pin.

In one embodiment, a pusher and pusher system include an inner element and an outer tubular sleeve. The outer sleeve includes a slot. A pin element extends through the slot and inner element to allow the inner element to displace relative to the outer sleeve.

In some embodiments, an implant delivery system utilizing a proximal handle is described. The proximal handle can either control the position of the outer delivery catheter/sheath, control the position of the pusher element, or control the position of a telescoping pusher member to allow the user to maintain precise control of a position of an implant during implant delivery.

In one embodiment, a proximal handle includes a user-actuated rotational mechanism such as a rotatable dial or thumbwheel. In one embodiment, the user-actuated rotational mechanism is connected to the sheath/catheter to displace the overlying sheath relative to the implant to deliver the implant. In one embodiment, the user-actuated rotational mechanism is connected to the implant pusher to displace the implant relative to the sheath to deliver the implant. In one embodiment, the user-actuated rotational mechanism is connected to a telescoping implant pusher to displace the implant relative to the sheath to deliver the implant.

In one embodiment, a proximal handle includes a user-actuated sliding mechanism. In one embodiment, the user-actuated sliding mechanism is connected to the sheath/catheter to displace the overlying sheath relative to the implant to deliver the implant. In one embodiment, the user-actuated sliding mechanism is connected to the implant pusher to displace the implant relative to the sheath to deliver the implant. In one embodiment, the user-actuated sliding mechanism is connected to a telescoping implant pusher to displace the implant relative to the sheath to deliver the implant.

In one embodiment, the handle includes an internal track so that the portion of the implant delivery system connected to the handle is confined to the area of the handle itself.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1A:
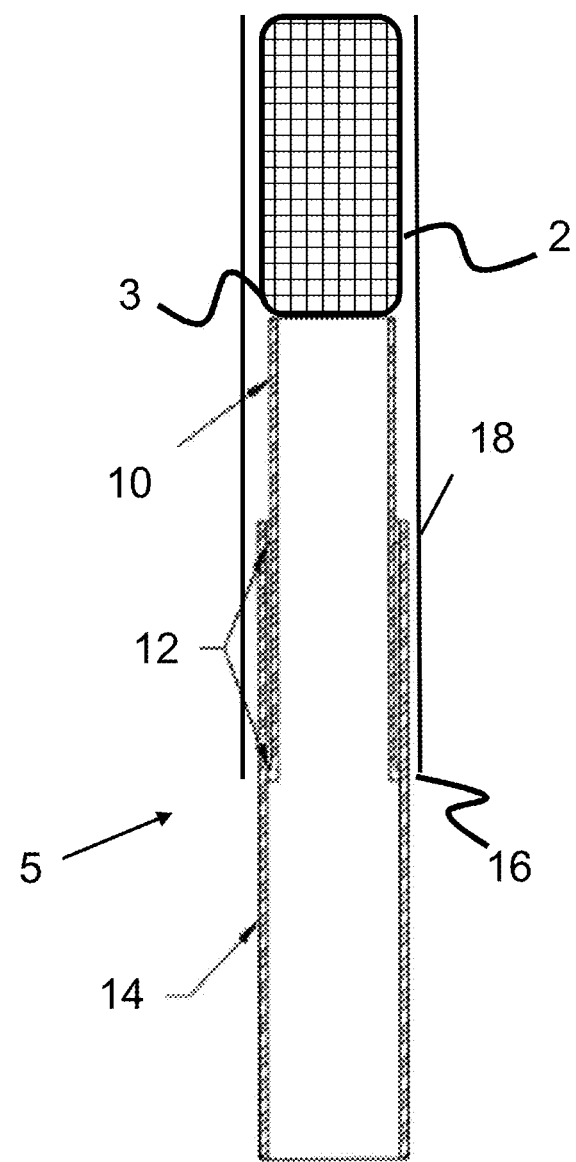
FIG. 1A illustrates a pusher utilizing an inner element and outer sleeve according to one embodiment.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Implants, in particular vascular prostheses such as stents and stent-grafts, can be used for a variety of reasons within the vasculature, such as propping open blood vessels to address calcification or thrombosis. These implants are typically delivered through a delivery catheter and are connected to a mechanical pusher which navigates the implant through the catheter and to the target treatment location. These pushers are usually long, especially when the implants are in harder-to-reach locations such as the neurovasculature since the pushers must be roughly or at least as long as the delivery catheter. For instance, some delivery catheters can be as long as about 150-200 centimeters. This length can introduce complications in designing, producing, and shipping/handling lengthy pushers/pusher systems.

The embodiments of the present invention that will now be presented utilize concepts which solve the problems outlined above. Some embodiments utilize an arrangement to reduce the overall length of the delivery pusher, for example by utilizing a telescoping pusher system to shorten the overall pusher profile. The telescoping pusher system would utilize an inner pusher element and outer pusher element where the inner pusher element partially slides within the outer pusher element to reduce the overall pusher length.

Please note, for the purposes of the description below the terms proximal and distal will be used. The proximal direction should be considered the direction towards the outside of the vasculature, while the distal direction should be considered the direction toward further placement within the vasculature. For instance, the proximal end of a catheter would sit outside of the body while the distal end of the catheter would sit within the vasculature when an interventional procedure is being conducted.

FIG. 1A shows a telescoping-type pusher system 5 utilizing an inner pushing element 10 and an outer pushing element or sleeve 14. A portion of inner element 10 is positioned within and overlaps with the outer sleeve 14 such that it projects distally beyond the outer sleeve 14. An implant 2, such as a vessel prosthesis like a stent or stent-graft is connected to the distal end of the inner pusher element 10 so that the inner element 10 moves, displaces, or positions the implant 2 distally within the vasculature. The advantage of a telescoping-type pusher system is that the overall pusher length is smaller, creating a smaller implant delivery profile.

The inner element 10 is elongated and has either a solid structure (e.g. a solid cylinder) or a hollow structure (e.g., a tube). Outer sleeve 14 is a tube having a lumen which accommodates the inner element 10. The inner element moves relative to the outer sleeve in a telescoping manner, such that it is can take on a first retracted position relative to the overlying outer pusher element/sleeve 14 and a second expanded/elongated position relative to the outer sleeve 14. The inner element 10 is either completely retractable within the outer sleeve 14 in its retracted configuration, or it partially extends from the outer sleeve in its retracted configuration. The inner element 10 is then displaceable so that it extends more fully from the outer sleeve 14.

The telescoping arrangement can be on various portions of the pusher, for instance just the distal portion of the outer sleeve 14 contains the telescopic arrangement with the inner element 10. Alternatively, a larger portion of the outer sleeve (e.g. substantially the entire length) utilizes the telescopic arrangement with the inner element 10. The telescoping length will also impact the pusher length—for instance, a smaller profile pusher would utilize a relatively short outer pusher sleeve 14 and a relatively long inner pusher 10, where the pusher has a smaller profile when the inner pusher is retracted within the outer sleeve. A larger profile pusher would utilize a relatively long outer pusher sleeve 14 and a relatively short inner pusher 10, where the pusher still has a relatively larger/longer profile even when the inner pusher is retracted within the outer sleeve. This telescopic arrangement can be accomplished in various different ways, which will now be described.

In one embodiment, inner pusher element 10 is slidable with respect to the overlying sleeve 14 and has a proximal protruding flange 16 that projects radially outward from the proximal end of the inner element 10. Outer pusher element/pusher sleeve 14 has a protruding stopper 18 that extends radially inwardly near the distal end of the sleeve 14 and is sized such that it laterally contacts and blocks the flange 16 from further distal movement when the inner element 10 is fully extended. The purpose of the flange 16 and stopper 18 is to create a mechanism to ensure that inner element 10 cannot slide distally past outer sleeve 14; thereby preventing the inner element 10 from further distal movement, thereby preventing inner element 10 from separating from outer sleeve 14. The distal portion of the inner pusher element 10 can also utilize a protruding flange so that the inner pusher element is prevented from completely entering the outer sleeve 14, meaning at least a portion of the inner pusher element extends distally beyond the outer sleeve 14.

Figure 1B:
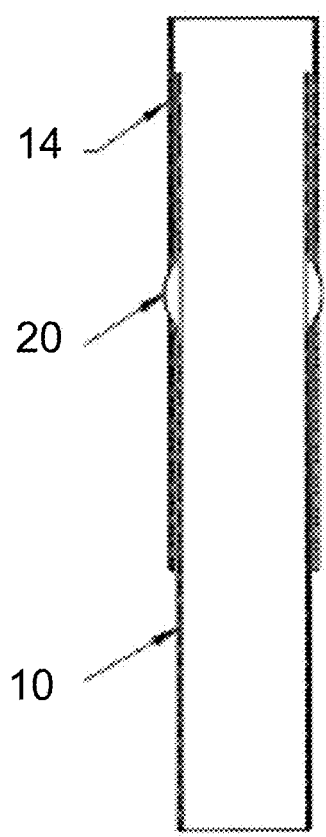
FIG. 1B illustrates a pusher utilizing an inner element and outer sleeve according to another embodiment.

FIG. 1B illustrates an alternative configuration involving the telescopic arrangement between inner element 10 and outer element/sleeve 14. In this arrangement, inner element 10 has a set of pins 20 that protrude radially outward and the outer sleeve 14 has one or more corresponding recesses facing radially inward to accommodate the pins 20 and form detents for the inner element 10. In one embodiment, these recesses would appear in multiple locations along the outer sleeve to provide multiple stopping points to fix the position of the inner pushing element 10 as it is pushed. The user will apply enough force to deform the pins (or deform the outer sleeve 14) in order to move the inner element 10 relative to the outer sleeve 14.

Figure 1C:
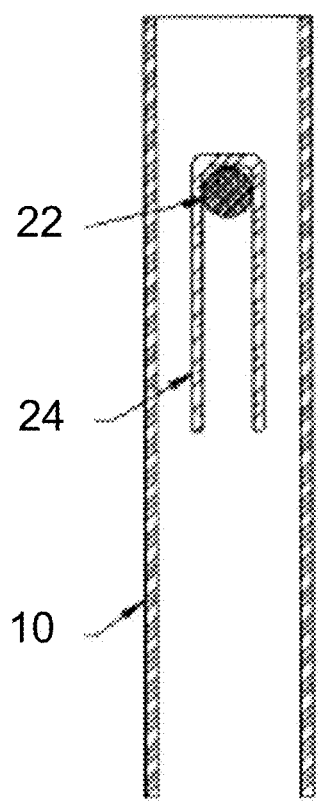
FIG. 1C illustrates a pusher utilizing an inner element and outer sleeve according to another embodiment.

FIG. 1C shows an alternative configuration where outer sleeve 14 contains a slot, channel, or cut-out section 24. A pin or slidable element 22 fixed on the outside of the inner element 10 passes through or engages the slot, such that the pin can freely traverse the length of the slot 24. The pin 22 also passes through a portion of the inner element 10, and in this way the pin can be used to allow translation of the inner element 10 relative to outer sleeve 14—meaning translation of the pin 22 will cause the inner element 10 to translate while the outer sleeve 14 remains stationary. The physician would move the pin, or a control mechanism connected to the pin would be used by the operating physician to move the inner pusher element 10 relative to the outer pusher sleeve 14, in order to displace the implant which is connected to the distal end of the inner element 10 as explained earlier. The flange/stopper arrangement shown and described above with reference to FIG. 1A can also be used with this embodiment to limit how far inner element 10 can advance relative to outer sleeve 14. Retracting or pulling the pin 22 will retract the inner element 10 relative to the sleeve 14, while pushing the pin distally will cause the inner element 10 to distally move relative to the sleeve 14. The outer sleeve slot containing the track for pin 22 can have both a proximal and distal end to control how much the pin 22 can translate both proximally and distally.

As described, the embodiments presented in FIGS. 1A-1C provide telescoping pusher mechanisms, whereby a pusher utilizes an inner element and an outer sleeve element that allow an inner element 10 to translate relative to the outer sleeve 10. The inner element 10 is connected to an implant 2, and in this way the implant 2 can be moved relative to the outer sleeve 14. In one embodiment, outer sleeve 14 and the proximal portion of the inner element 10 are contained within a delivery handle where the user interacts with some actuation mechanism (e.g., a rotational dial or linearly displaceable slider element) to translate the inner pusher element 10 relative to the outer pusher sleeve 14. For example, the actuation mechanism is connected directly to the inner sleeve so that engaging the actuation mechanism (e.g. moving the dial or slider) will then displace the inner pusher element 10 relative to the outer sleeve 14. In one example involving the embodiment of FIG. 1C, the actuation mechanism is connected to the pin element 22, so that moving the actuation mechanism in turn displaces the pin 22 to thereby distally advance the inner element 10 relative to the stationary outer sleeve 14.

Another challenge when delivering implants (e.g. stents and/or stent grafts) is achieving proper placement within the particular vascular region of interest. Most delivery systems utilize a push-pull technique where a physician either holds a mechanical pusher still while manually retracting an overlying sheath/catheter to deploy the implant or holds the overlying sheath still while distally pushing the mechanical pusher connected to the implant to thereby deploy the implant, or performs some combination of the two techniques. The pusher and sheath can move during the implant delivery process making proper placement of an implant difficult. This problem is magnified when the implant is being deployed in tortuous anatomy, or in smaller blood vessels such as those of the neurovasculature. The following embodiments address these issues by providing a proximal handle mechanism to control advancement and deployment of the implant, thereby offering enhanced control of the implant during the delivery process.

Unlike the previous embodiments which focused on a telescoping pusher mechanism to advance an implant and thereby reducing the overall delivery pusher profile, the following handle-focused embodiments will utilize a handle connection mechanism which either: a) directly connects to the pusher to advance/retract the implant, or b) directly connects to the sheath/catheter overlying the pusher and implant to retract the sheath to deploy the implant. However, certain handle embodiments are usable with the telescoping pusher embodiments describe above.

Figure 2A:
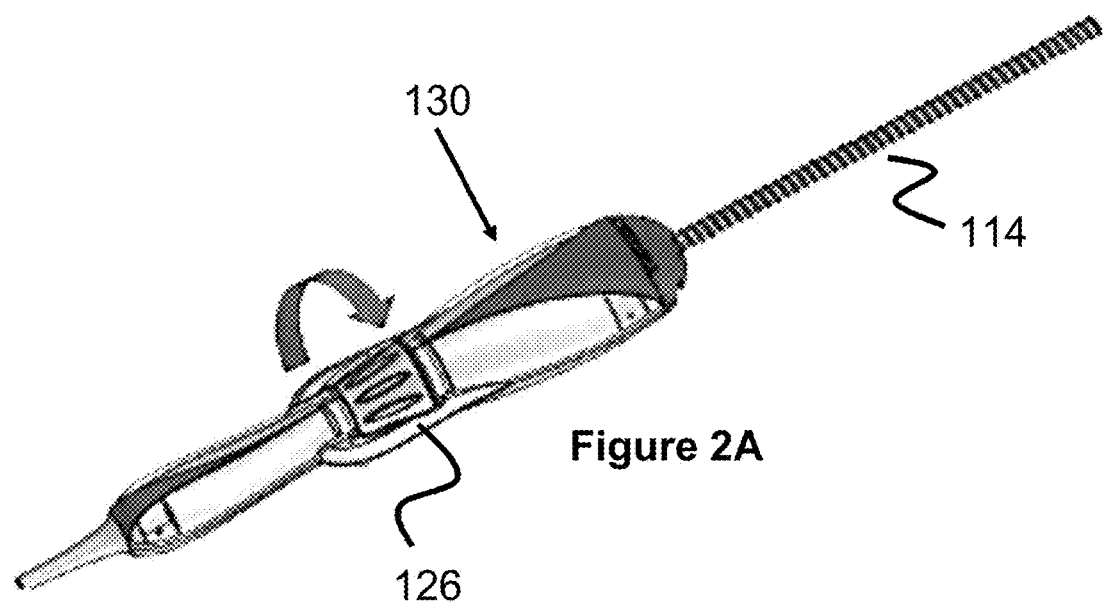
FIG. 2A illustrates a handle assembly with a rotational mechanism according to one embodiment.
Figure 2B:
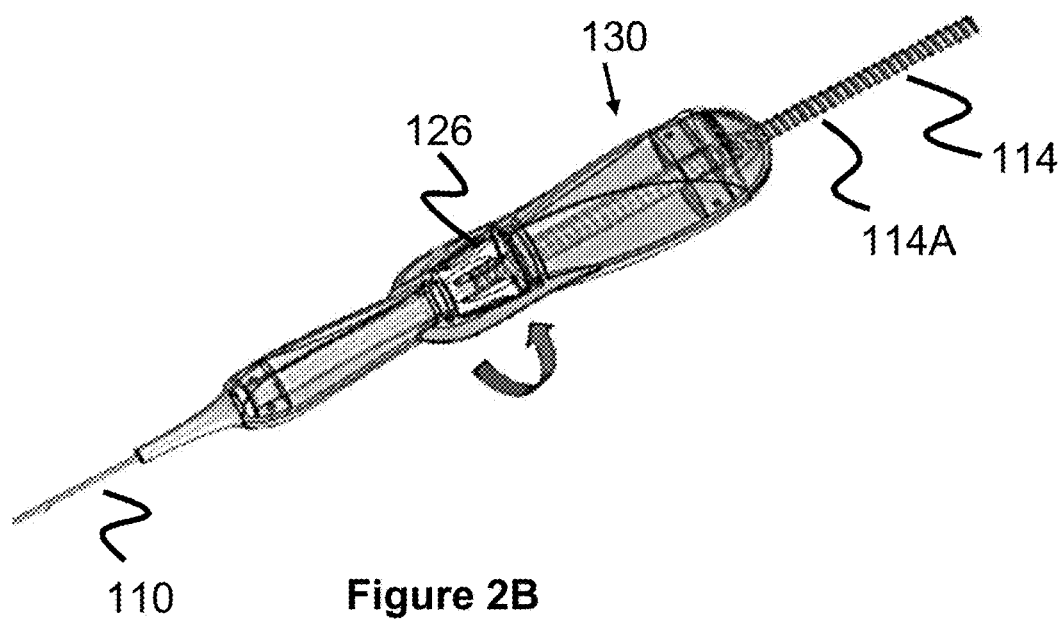
FIG. 2B illustrates a handle assembly with a rotational mechanism according to one embodiment.

FIGS. 2A-2B illustrate a handle assembly 130 that is used as part of a broader implant delivery system. The implant delivery system includes a pusher component used to displace an implant. As shown in FIGS. 2A-2B, the pusher components comprise two sections, a first proximal section 114 and a second distal section 110 (shown in FIG. 2B). In some embodiments, the proximal pusher section 114 overlies the distal section 110 and therefore the proximal section 114 may function and be considered like a sleeve while the distal section 110 may function and be considered like an inner element.

The pusher structure comprising elements 114 and 110 can take on a variety of configurations. In one embodiment, proximal section 114 and distal section 110 are part of the same unitary pusher structure, where proximal section 114 contains a threaded region to engage with a corresponding mechanical structure on user-actuated handle mechanism 126 (which will be explained in more detail later) in order to advance and retract the pusher. Therefore, the broader pusher is one unitary structure where a proximal section 114 is threaded and a distal section 110 is not threaded, where the distal end of this distal pusher section 110 is then directly connected to the implant (not shown). In another embodiment, proximal pusher section 114 and distal pusher section 110 are two different pieces which are attached together in a non-telescoping manner—for instance, the proximal pusher section 114 is a tube or sleeve with an inner lumen and distal or inner pusher section 110 is directly attached to an interior of the proximal pusher section. In one embodiment, the proximal pusher section 114 and distal pusher section 110 are both proximally attached at the same location (meaning, the distal pusher section 110 is attached to the proximal end of the proximal pusher section 114), and distal pusher section 110 is longer so that it distally exits the proximal pusher section 114—in this manner, engaging and moving element 114 will move both sections 110 and 114. Regardless of whether the proximal 114 and distal 110 pusher sections are unitary or attached together, displacement of section 114 will also displace distal section 110—either because they are part of the same unitary structure, or because they are directly attached together. The handle contains a user-actuated control mechanism to translate the broader pusher (including pusher sections 114 and 110), which will now be explained.

In one embodiment, the handle includes a user-actuated control mechanism to translate the pusher portion 114, whereby the control mechanism directly engages the pusher portion 14. The user engages a rotational dial 126 which is connected to the pusher portion/section 114. The dial is configured to rotate around a longitudinal axis of the assembly 130, allowing for easy rotation via a user's fingers and thumb. The pusher section 114 has a surface 114A, for example helical male threads, which engage a corresponding surface (e.g. inwardly-radial mating threads) located on the inside of the dial 126. In this way, rotation of the dial 126 allows the two engaged threads to translate the connected pusher portion 114 either distally or proximally. Since distal pusher section 110 is connected to proximal pusher section 114 (either due to direct connection, or due to being part of the same unitary structure), the distal pusher section 110 will also longitudinally translate as the proximal pusher section 110 translates. In one example, rotating the dial 126 clockwise can move the pusher and connected implant 2 forward, while rotating the dial 126 counterclockwise can move the pusher and connected implant backwards; though these configurations can be inverted such that rotating the dial counterclockwise will advance the pusher and implant, and vice-versa.

The handle concept of FIG. 2A can also be modified to work with a telescopic pusher system, like the one of FIG. 1C. For instance, the proximal/overlying pusher element 114 would function like the outer sleeve of FIG. 1C while the distal/inner pusher element 110 would function like the inner pusher element 10 of FIG. 1C. The rotational dial 126 would connect to the sliding pin 22 (in various mechanical connections known in the art to translate rotational motion to translational displacement) so that rotating the dial 126 will either advance or retract the pin, to thereby advance or retract the inner telescoping pusher element. Alternatively, the inner and outer elements can also utilize a rotational engagement mechanism (e.g. threads) so that rotating the dial 126 will advance the distal/inner pusher element. This embodiment could further be used on a pre-loaded implant system, where a stent or stent-graft is preloaded at a distal portion of an overlying sheath or catheter, and the user simply engages the dial to translate the pin 22 to allow the telescoping distal pusher element to advance the implant out of the distal end of the catheter.

As shown in FIG. 2A, the pusher portion 110 proximally extends from the handle 130. Depending on where the implant is being used, the pusher can be rather long. For instance, many pushers can be about 150-200 centimeters in length. Implants that are used in the neurovasculature have a fairly lengthy associated pusher length since the delivery catheter has to span the region from the femoral artery (leg region) all the way to the neurovasculature (brain region), thereby spanning most of the length of the human body. In order to not make an oversized delivery handle that would be too large to comfortably operate, an initial configuration of the proximal pusher section 114 would proximally extend from the handle. As the pusher and pusher section 114 is advanced, the proximal pusher section will move more distally towards the handle as distal pusher section 110 also advances—as shown in FIG. 2B. Other embodiments which will be discussed later avoid this by providing an internal track mechanism whereby the pusher structure is completely confined to the handle. In one embodiment, the implant is pre-placed at a distal section of the catheter and the handle is only used to advance the implant out of the distal end of the catheter—in this embodiment, the proximal pusher structure may not need to proximally extend beyond the handle since the implant will not need to navigate the entire catheter (instead, it will only need to navigate the distal portion of the catheter since it is preplaced at the distal section of the catheter). Alternatively, where the implant is meant to be used in a closer treatment location relative to the point of access (for instance, a stent or stent graft used to treat leg calcification where access is gained through the femoral artery), then the pusher profile will also be smaller since the implant will not need to navigate so far through the vasculature to reach the target region.

Figure 3:
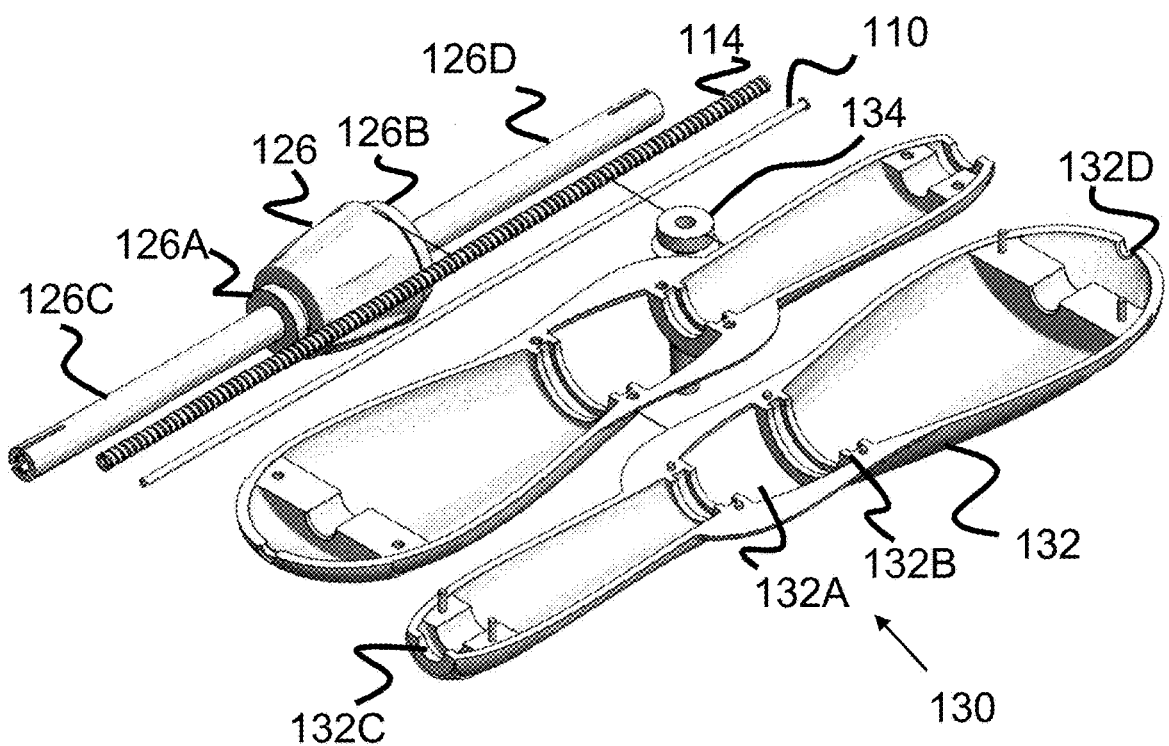
FIG. 3 illustrates an exploded view of a handle assembly according to one embodiment.
Figure 4:
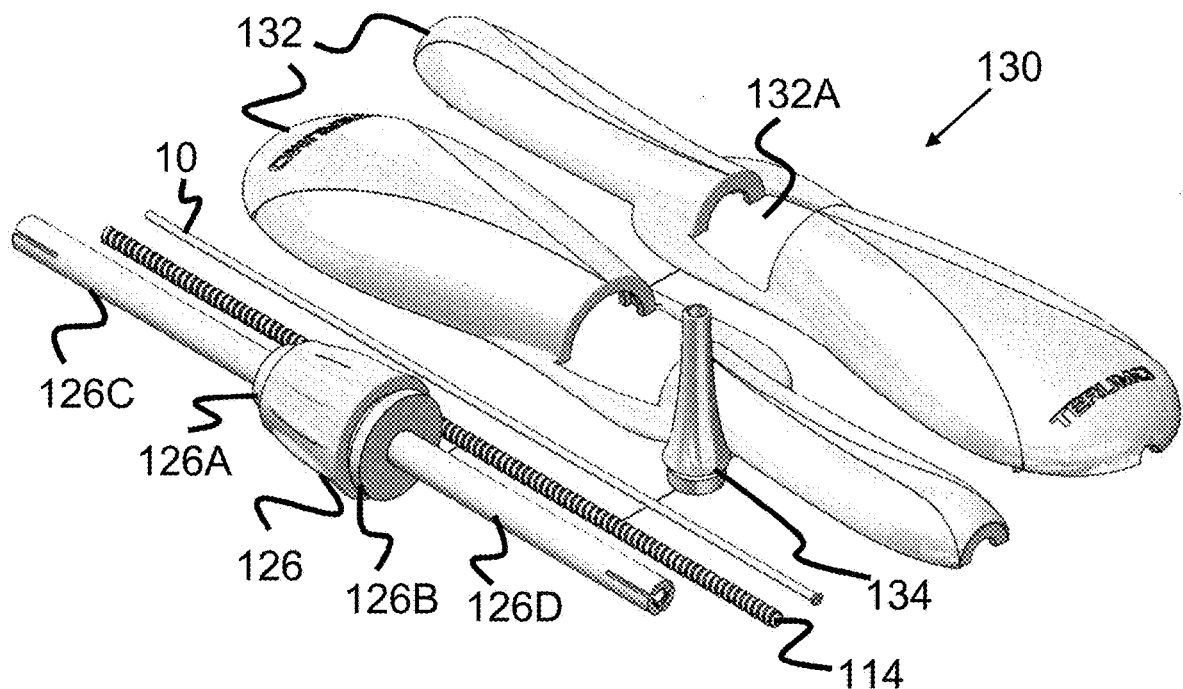
FIG. 4 illustrates an exploded view of a handle assembly according to one embodiment.

As seen best in the exploded views of FIGS. 3 and 4, the handle assembly 130 includes two outer shell components 132 that connect to and engage each other to form a complete housing. The shell components 132 form an inner cavity with a proximal port 132C and distal port 132D through which the pusher section 114 moves through. The proximal port 132C preferably includes a recess sized to capture the end of the strain relief tip 134, which also has a passage therethrough for the pusher sections 114 and 110. Note, in FIGS. 3 and 4, the proximal pusher section 114 and distal pusher section 110 are shown as two separate elements, here the two sections would be connected together at some distal location along threaded pusher section 114, such that engaging and moving pusher section 114 via the handle control mechanism 126 will also displace the connected distal pusher section 110 in a non-telescopic manner. For note, as discussed above, the pusher can take on various configurations including a unitary structure with a threaded proximal portion 114 and a non-threaded distal portion 110. Alternatively, the pusher sections 110 and 114 can have a telescoping functionality, as described in the discussion above referencing FIGS. 1C and 2A-2B.

The dial 126 includes proximal and distal elongated portions 126C and 126D to help maintain the dial within the handle assembly 130. Additionally, ridges 126A and 126B fit within recesses 132B on each end of the knob aperture in the shells 132, which further maintain the exposed thumb engagement portion of the dial 126 in a desired location. The dial 126, and its proximal and distal elongated portions 126C and 126D have a passage therethrough which has a thread on its inner surface that is configured to engage with the thread 114A on the proximal pusher section 114. Preferably, the proximal pusher section 114 is further prevented from rotating within the handle assembly so that when the dial 126 is rotated around it, the threads of its inner passage cause the pusher section 114 to longitudinally move. For example, this may be accomplished by including a groove along the side of the pusher section 114 and including a feature on the inside of the shell components 132 that engages the groove. Alternately, the pusher section 114 may include a raised portion that slides within a groove of the housing.

The delivery handle of FIGS. 2-4 has so far been generally described with a fixed, non-telescoping pusher mechanism. For instance, the distal pusher element 10 can be welded or connected directly to proximal section 110, or alternatively can utilize the pin configuration 20 of FIG. 1B where only one recess is used such that the distal pusher element 110 is contained within part of proximal section 110 and is fixed relative to the proximal section 110. Alternatively, the inner element/outer sleeve interface can include one of the concepts of FIGS. 1A and 1C to allow a small degree of movement between the two, thereby having a partial telescopic functionality. For example, the distal portion of the larger proximal pusher section 114 includes the stopper of FIG. 1A and the proximal end of distal pusher section 110 sits within the distal-most section of the larger pusher section 114, so that there is a small degree of movement between the inner sleeve and outer sleeve. Alternatively, the configuration of FIG. 1C can be used (as discussed above) where the distal section of pusher section 114 contains a slot 24 and the proximal end of distal/inner pusher section 110 includes a pin and the pin can move the length of the slot to advance the distal pusher section 110 relative to the proximal pusher section 114.

Figure 5:
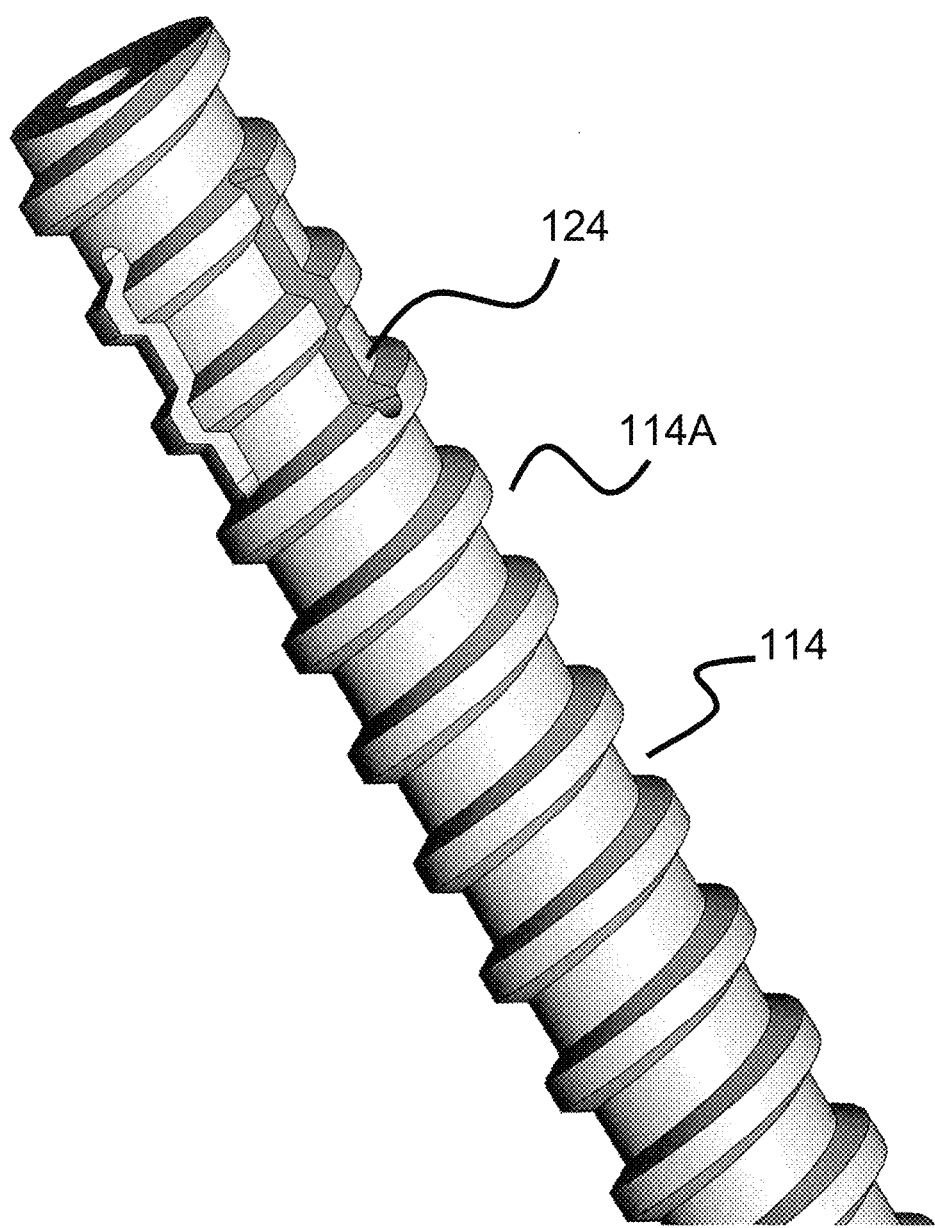
FIG. 5 illustrates an outer sleeve with a groove according to one embodiment.
Figure 6:
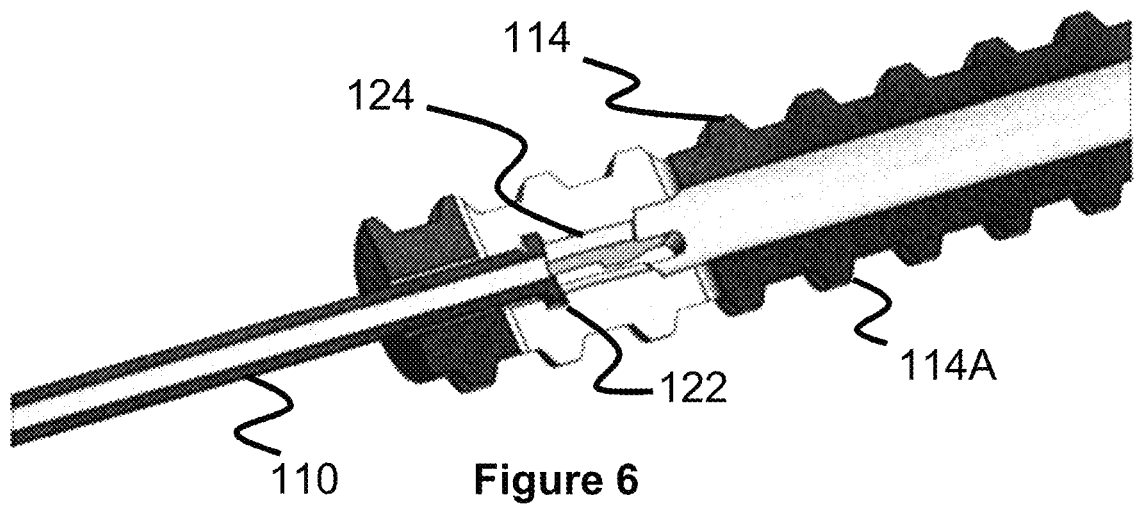
FIG. 6 illustrates an outer sleeve with a groove according to one embodiment.
Figure 7:
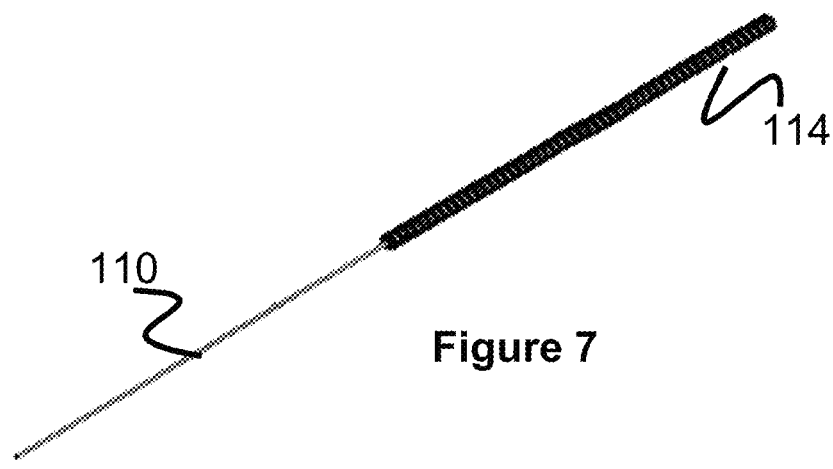
FIG. 7 illustrates an outer sleeve according to one embodiment.
Figure 8:
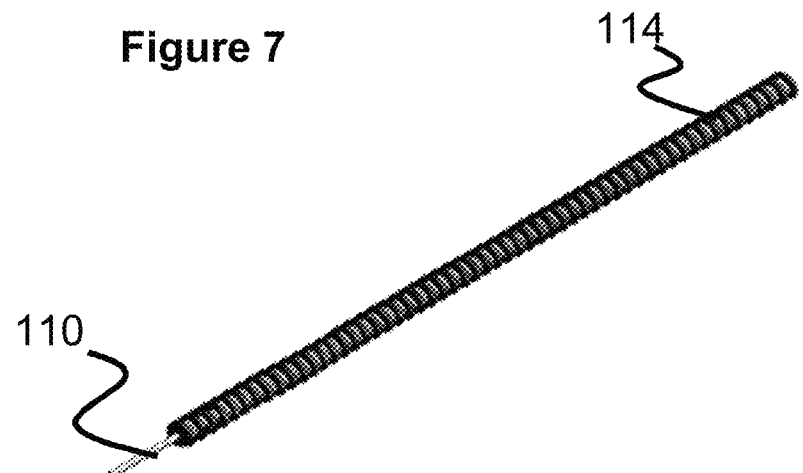
FIG. 8 illustrates an outer sleeve according to one embodiment.

FIGS. 5 and 6 illustrate one example embodiment of the proximal threaded pusher section 114 with outer threads 114A that also includes a slot 24, as discussed with regard to FIG. 1C, which allows one or more pins 22 on the inner element 10 to engage and thereby slide within the slot 24. While the slot 24 in FIG. 5 is illustrated as being relatively short, it may also extend substantially all or most of the length of the pusher section 114, thereby allowing most of the distal pusher section 110 to be retracted within the proximal pusher section 114, as seen in FIGS. 7 and 8. With this embodiment, the proximal pusher section 114 would function like sleeve 14 of FIG. 1C while the distal pusher section 110 would then function like inner pusher portion 10 of FIG. 1C.

In other embodiments, the handle control mechanism 126 of FIGS. 2-4 would not engage with the pusher at all. Instead, the delivery sheath/catheter overlying the implant would utilize a threaded section on at least a proximal section of the catheter. Rather than using the control mechanism 126 to displace the pusher, the control mechanism would be used to retract the sheath (e.g. rotating the knob in one direction to proximally retract the sheath). In this manner, the implant would be deployed by proximally retracting the sheath. The user could use a separate internal pusher (e.g. where element 110 of FIG. 3 now takes on the role of the pusher while element 114 functions as the sheath or delivery catheter) to push the implant through the overlying catheter. In one embodiment, the implant delivery system utilizes an implant pre-placed at a distal section of the delivery catheter (the delivery catheter functioning as element 114 in this particular embodiment). The user would then engage the handle control mechanism 126 to retract the sheath to thereby expose and deliver the implant connected to a distal end of the pusher (e.g., element 110 for the purposes of FIGS. 2-4).

In one embodiment, the handle assembly 130 is used as part of a broader vascular prosthesis delivery system. For example, a stent or stent-graft delivery system where the implant is pre-packaged within the distal section of a delivery catheter and the handle is used to mechanically move the implant solely through the distal portion of the catheter for delivery within the vasculature, as discussed above. One such system is described in US Publication Nos. 20170079820 and 20170079812, both of which are incorporated by reference in their entirety. Additional example embodiments are discussed in greater detail later in this specification with regard to FIGS. 16-23.

Figure 9:
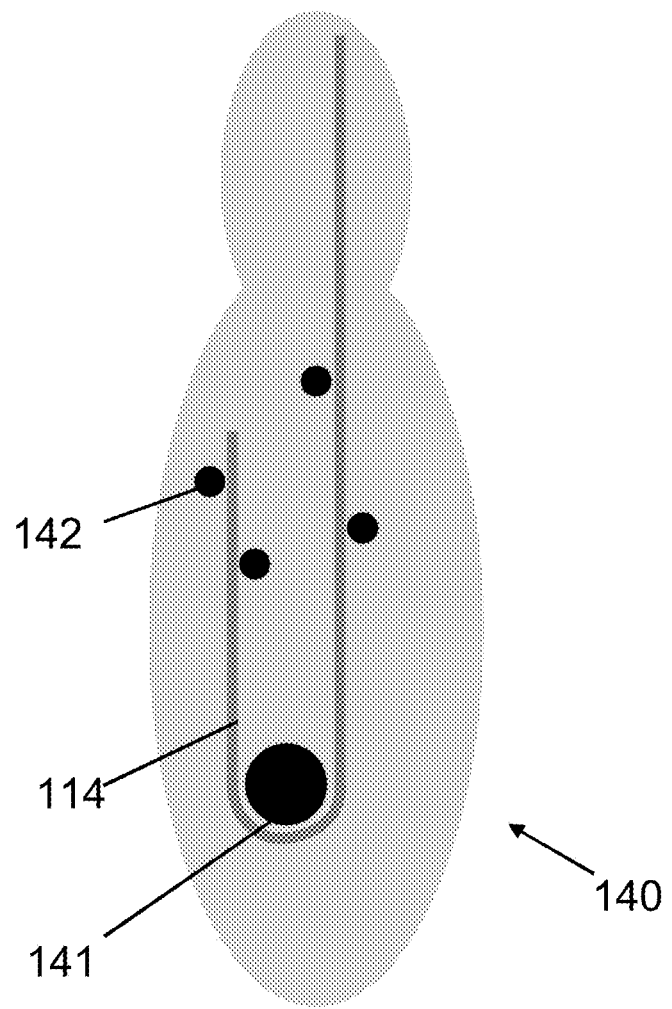
FIG. 9 illustrates a handle assembly with an internal track according to one embodiment.

Earlier parts of the description discussed FIGS. 2A-2B and how in some embodiments, the proximal pusher section 114 (or alternatively, sheath 114 where the delivery catheter/sheath instead utilizes the threaded engagement components to move with respect to the handle) needs to proximally exit the handle in certain embodiments. FIG. 9 shows a handle utilizing an internal track mechanism within the handle assembly 40, which can be used to prevent the assembly 114 from projecting beyond the handle (note: for the purposes of this embodiment, since the track is used to contain element 114 whether it is a proximal pusher element or sheath, 114 will simply be referred to as an assembly to be inclusive). The internal track contains one or more bends to contain assembly 114, such that the assembly is confined to the track and will therefore not need to exit the handle. As discussed earlier, since the length of the delivery catheter can be fairly long in certain procedures, it would be hard to design a handle large enough to contain the entire implant delivery structure. However, with this internal track concept, the track keeps the assembly 114 within the handle. In this embodiment, a rotational element 141 is used as part of a bending track which contains the assembly 114. A number of mechanical rollers 142 can be placed on either side of the track to move the outer sleeve/assembly 114 in response to the rotational knob movement, and the bending track would keep the assembly 114 fully within the handle structure 140.

In one embodiment, the rollers 142 and rotational element 141 are connected to the user engagement mechanism 126 (see FIGS. 2-4) so that rotating or engaging the user engagement mechanism will also engage the rollers to move the assembly 114 along the internal track. In another embodiment, rotating or engaging the user engagement mechanism 126 will move the assembly 114 and this movement of the assembly causes the adjoining rollers (141, 142) to also rotate thereby helping to move along the rest of the assembly. In the example shown, a simple U-shaped track is shown however different track shapes can be used, including more serpentine track structures. The biggest variables affecting the track shape include the size of the handle and the size of the assembly 114 that needs to be accommodated; therefore, a smaller handle 140 or a larger assembly 114 will likely require a more serpentine-type track structure with more bends, while a larger handle 140 or smaller assembly 114 will likely require a simpler track structure. Please note, though the term track structure is used, this can utilize either: a) the concept of a recessed or built-in structure that the assembly 114 sits into, or b) the concept of a path created between the various rollers 142 thereby creating an overall path that accommodates assembly 114.

Figure 10:
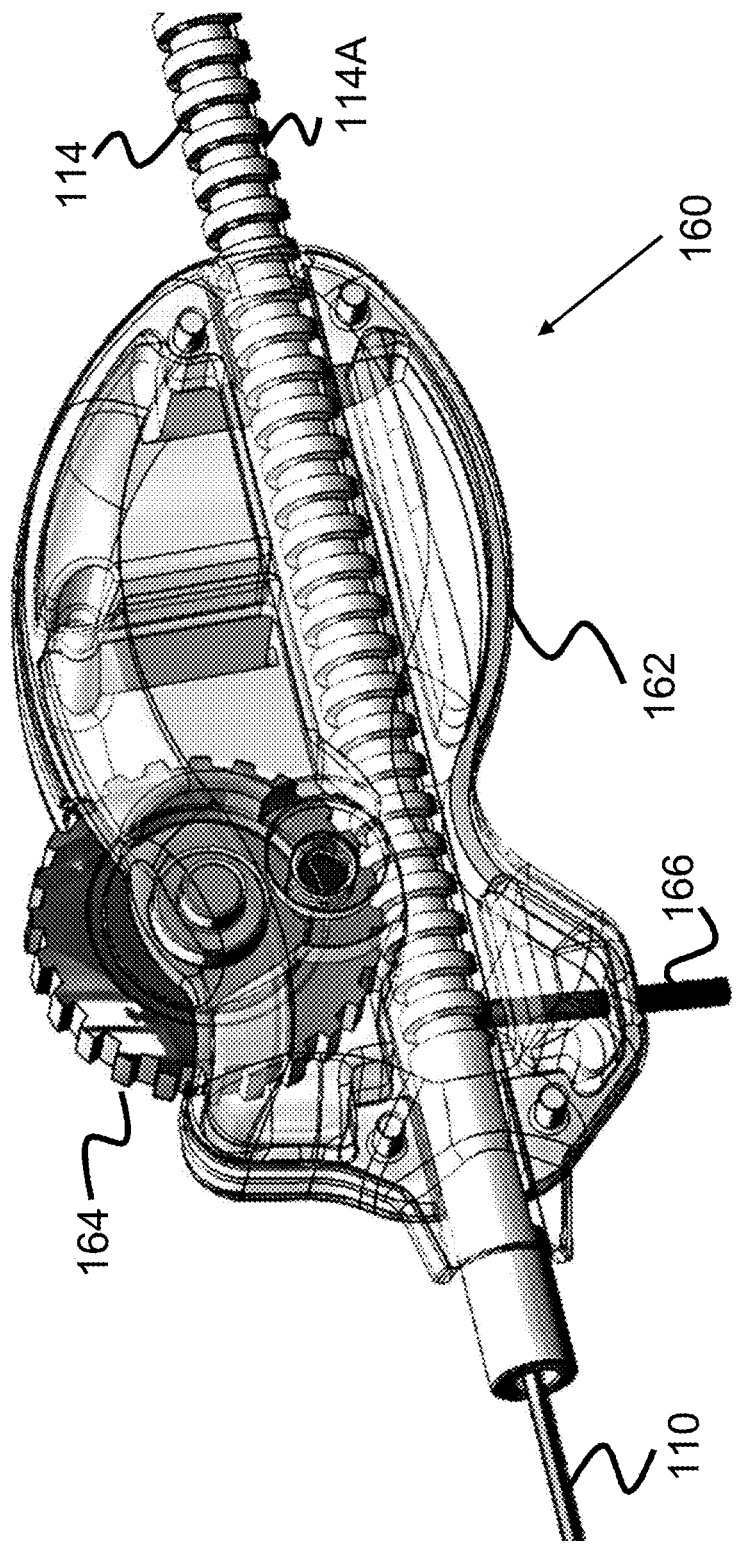
FIG. 10 illustrates a handle assembly with a rotational mechanism according to one embodiment.

Other handle mechanism embodiments are also contemplated. FIG. 10 illustrates another embodiment of a handle assembly 160 that functions generally similar to the handle embodiment of FIGS. 2-4. The handle assembly 160 longitudinally advances/retracts a proximal pusher portion 114 and attached/connected/or integral distal pusher portion 110 of the pusher. The handle assembly 160 includes an outer housing 162 with a passage therethrough that is sized to allow longitudinal movement of the proximal pusher section 114 through it. Unlike the dial of the previously discussed handle assembly 130 that rotates around a longitudinal axis of the assembly, the thumbwheel 164 rotates perpendicularly to the longitudinal axis of the assembly 160. Further, the thumbwheel 164 includes a plurality of gear teeth around its circumference that are sized and positioned to engage the geared surface 114A of the pusher portion 114. Unlike prior embodiments that may have a helical thread on the outer surface 114A, this embodiment has non-helical, circumferential gear teeth. In this respect, rotating the thumbwheel 164 causes the pusher portion 114 to move longitudinally relative to the housing 62. Optionally, the handle assembly 160 includes a locking pin 166 that passes through the housing 162 and engages the threaded surface 114A of the pusher section 114, preventing it from moving. The user may then remove this pin 166 at a desirable time to allow movement of the pusher section 114. In one embodiment, as discussed in the earlier handle embodiments, the pusher comprises a larger proximal section 114 which contains the gearing interface, and a smaller distal pusher section 110 which actually connects to the implant. The proximal 114 and distal 110 pusher sections are connected similar to the handle embodiment of FIGS. 2-4 (either through mechanical attachment, or by being a unitary pusher which two differently shaped regions)—in any of the various ways described above involving the discussion of FIGS. 2-4. These attachment configurations include (but are not limited to): a) the distal pusher section 110 being attached to a distal portion of the proximal pusher section 114, or b) distal and proximal pusher sections being a unitary structure machined to have a different shape in each region, or c) the distal pusher region 110 spanning the entirety of the proximal pusher section 114 and distally exiting the proximal pusher section 114 and where the two pusher sections are connected together at the same location at the proximal end of proximal pusher section 114. The alternative configurations discussed above to allow a slight or fully telescoping functionality to the proximal 114 and distal 110 pusher sections can also be used on this embodiment. For instance, the pin concept of FIG. 1C can be used where the pin element is underneath the gearing interface 114/114A so that the pin element 22 is moved to distally translate a distal inner telescoping pusher element, to thereby advance the implant which is connected to the inner telescoping pusher element.

In one embodiment, section/element 114 takes on the form of the delivery sheath or delivery catheter where a portion of the sheath has the gearing mechanism, rather than section 114 being a portion of the delivery pusher. Element 110 would then be considered the delivery pusher which is distally attached to the implant. The user would manipulate the pusher separately from the sheath by pushing the pusher through the sheath until the implant is in a distal part of the sheath. When it comes time to deploy the implant, the user would interface with the thumbwheel 164 to retract the sheath element 114 thereby exposing the implant. In one embodiment, the implant is pre-placed within a distal section of the sheath and the user would track the sheath/catheter though the vasculature to the target treatment location, and then retract the sheath through rotating the thumbwheel 164 to deploy the implant.

Figure 11:
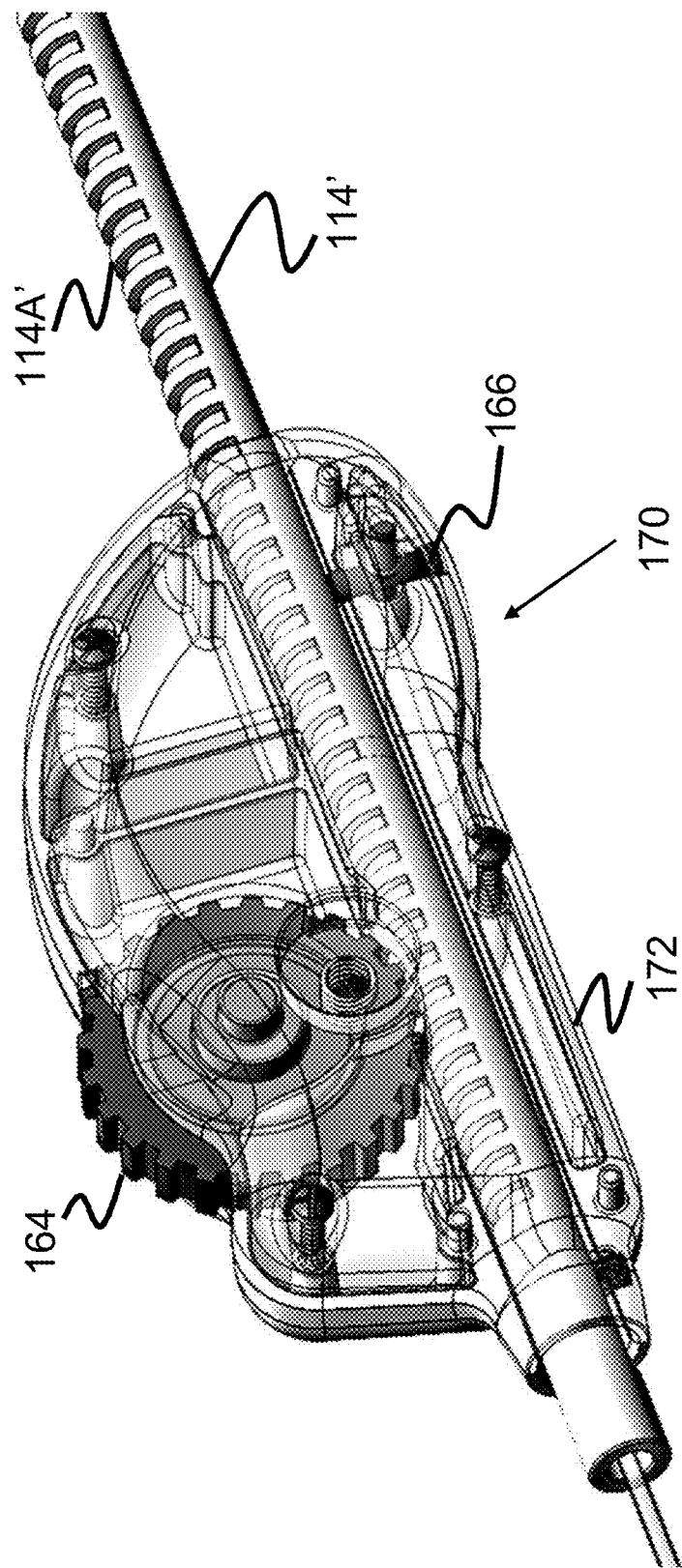
FIG. 11 illustrates a handle assembly with a rotational mechanism according to one embodiment.
Figure 12:
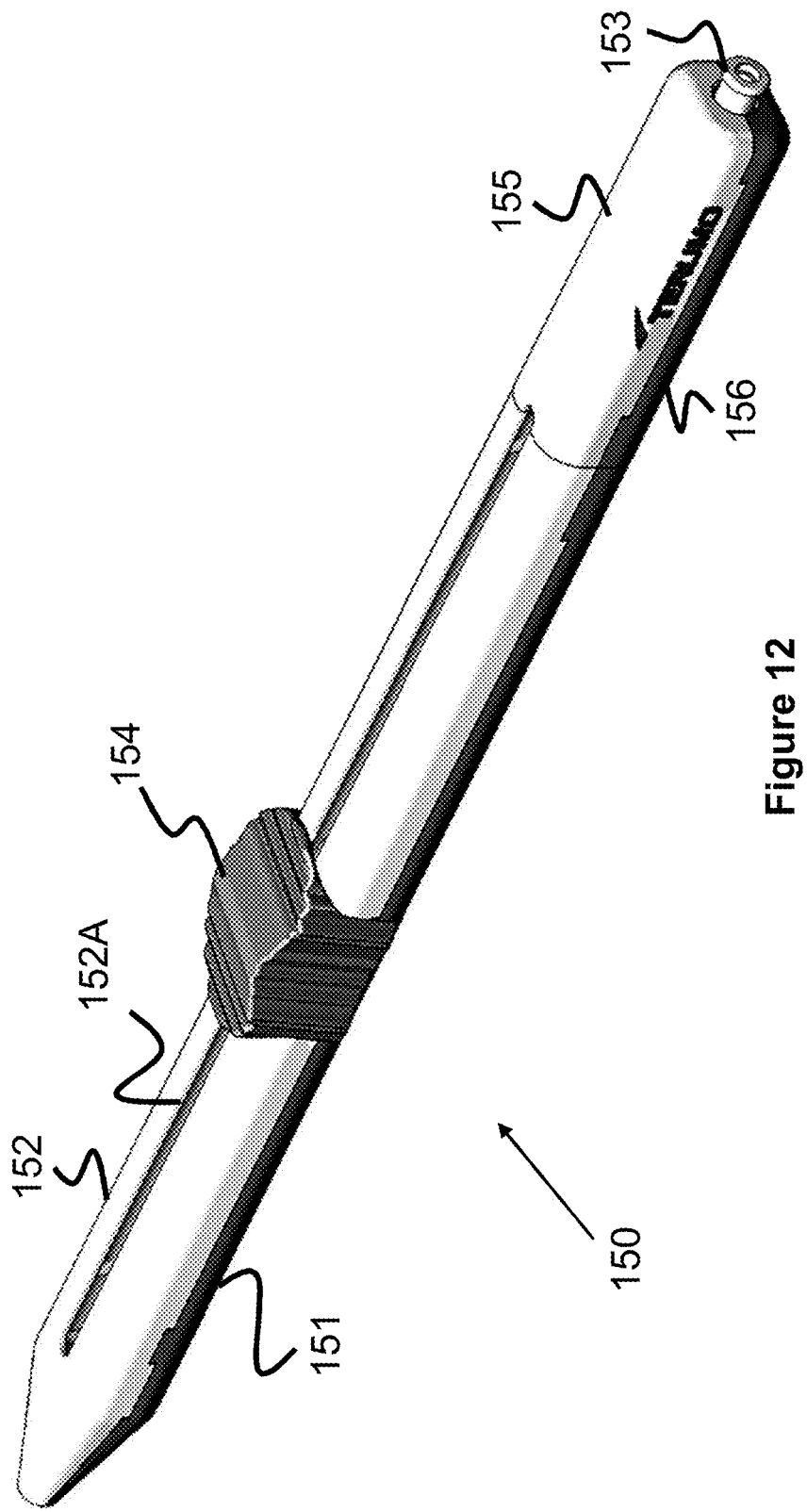
FIG. 12 illustrates a handle assembly with a sliding mechanism according to one embodiment.
Figure 13:
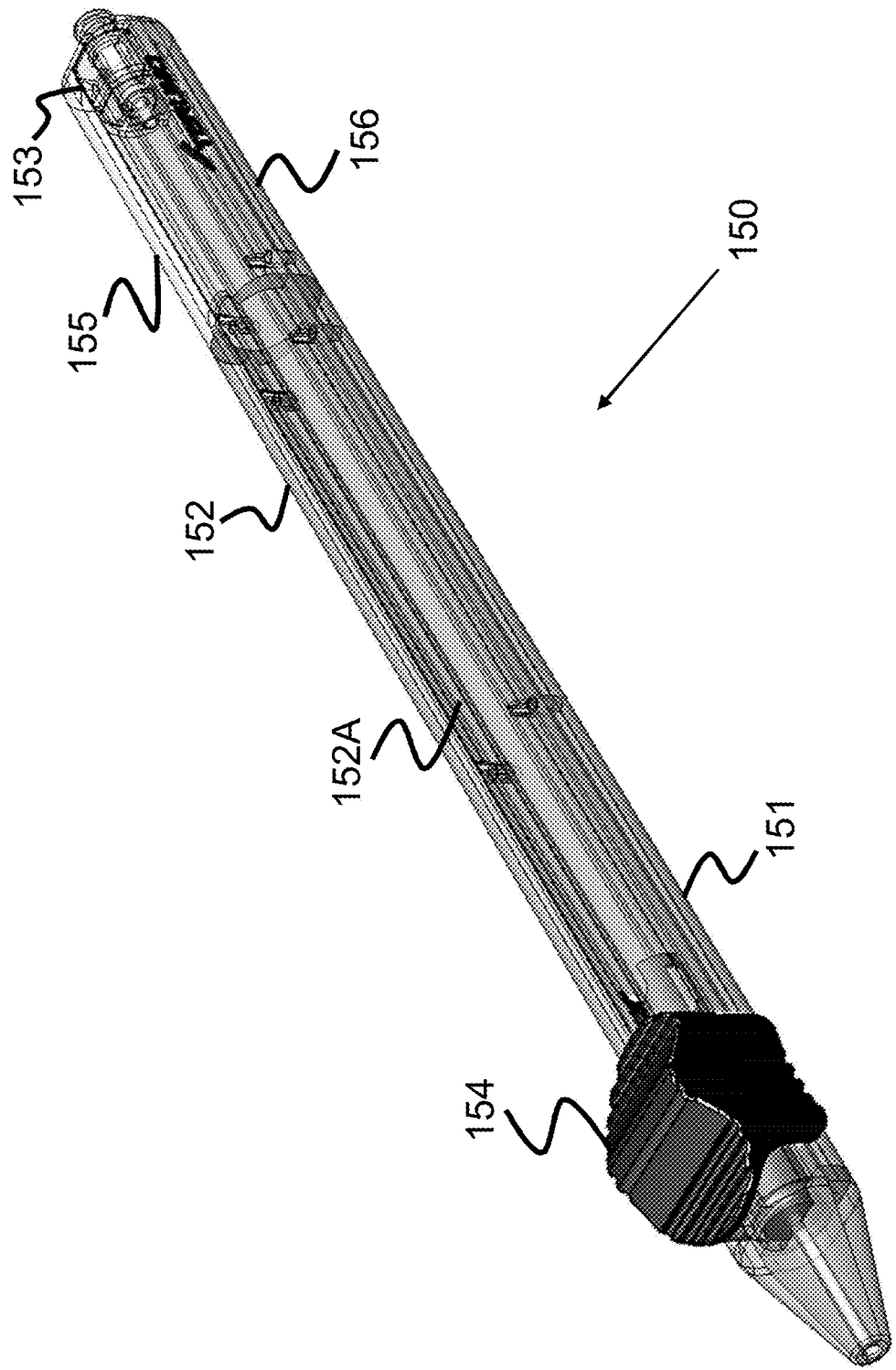
FIG. 13 illustrates a handle assembly with a sliding mechanism according to one embodiment.

FIG. 11 illustrates an alternate embodiment of a handle assembly 170 that is generally similar to the previously described assembly 160. However, the lower portion of the housing 172 is a generally uniform shape, as opposed to the lower "bump" on assembly 160. Additionally, this embodiment illustrates the use of a pusher section 114' having a longitudinally uniform or symmetrical gear track/surface 14A' on only one side of the pusher section 14', as opposed to the helical thread of surface 114A in prior examples or the circumferential, symmetrical gear teeth of assembly 160. Like the previous embodiment(s), section 114' can alternatively be the sheath or catheter instead of a section of the pusher.

Figure 14:
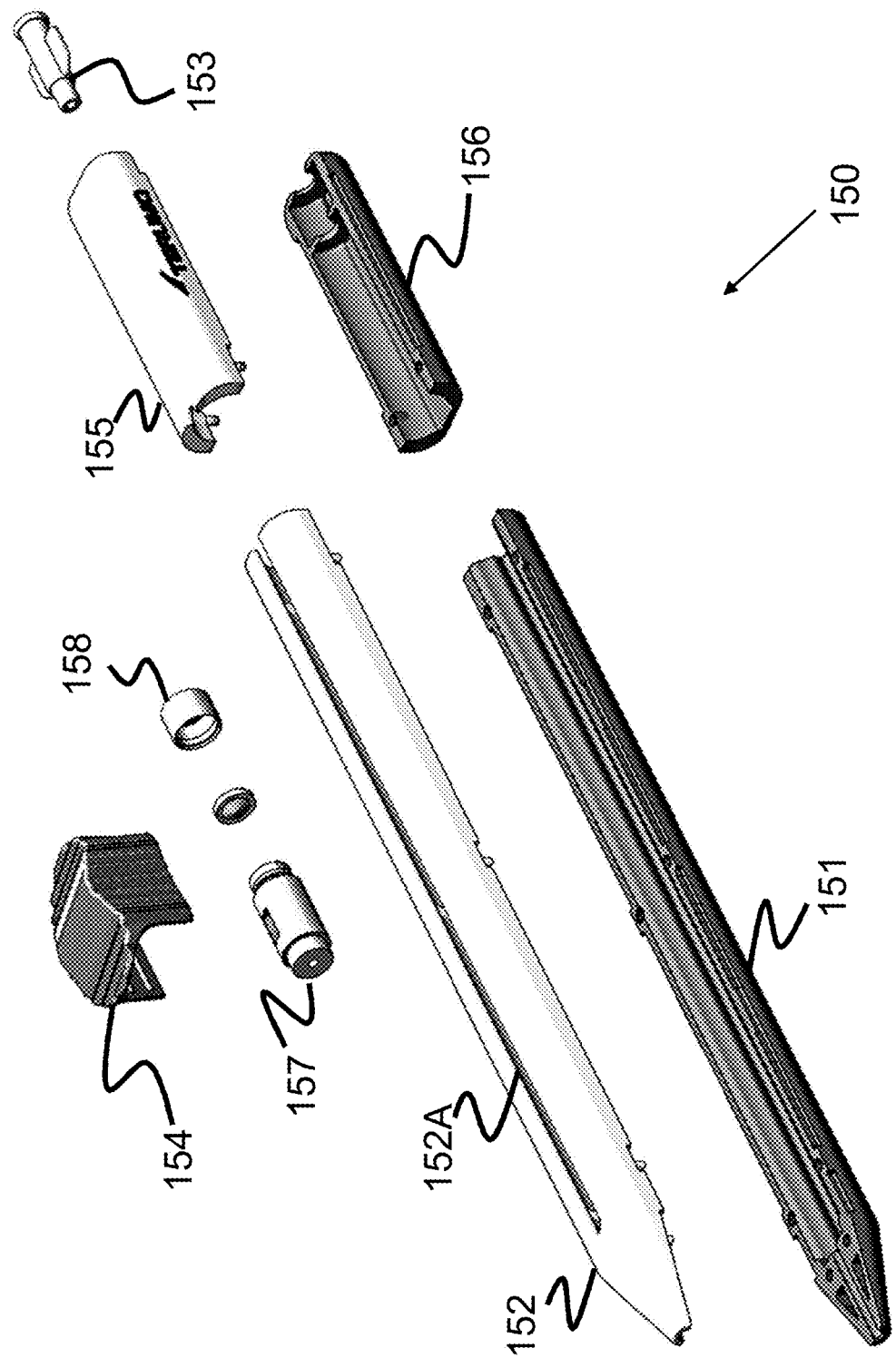
FIG. 14 illustrates an exploded view of a handle assembly with a sliding mechanism according to one embodiment.
Figure 15:
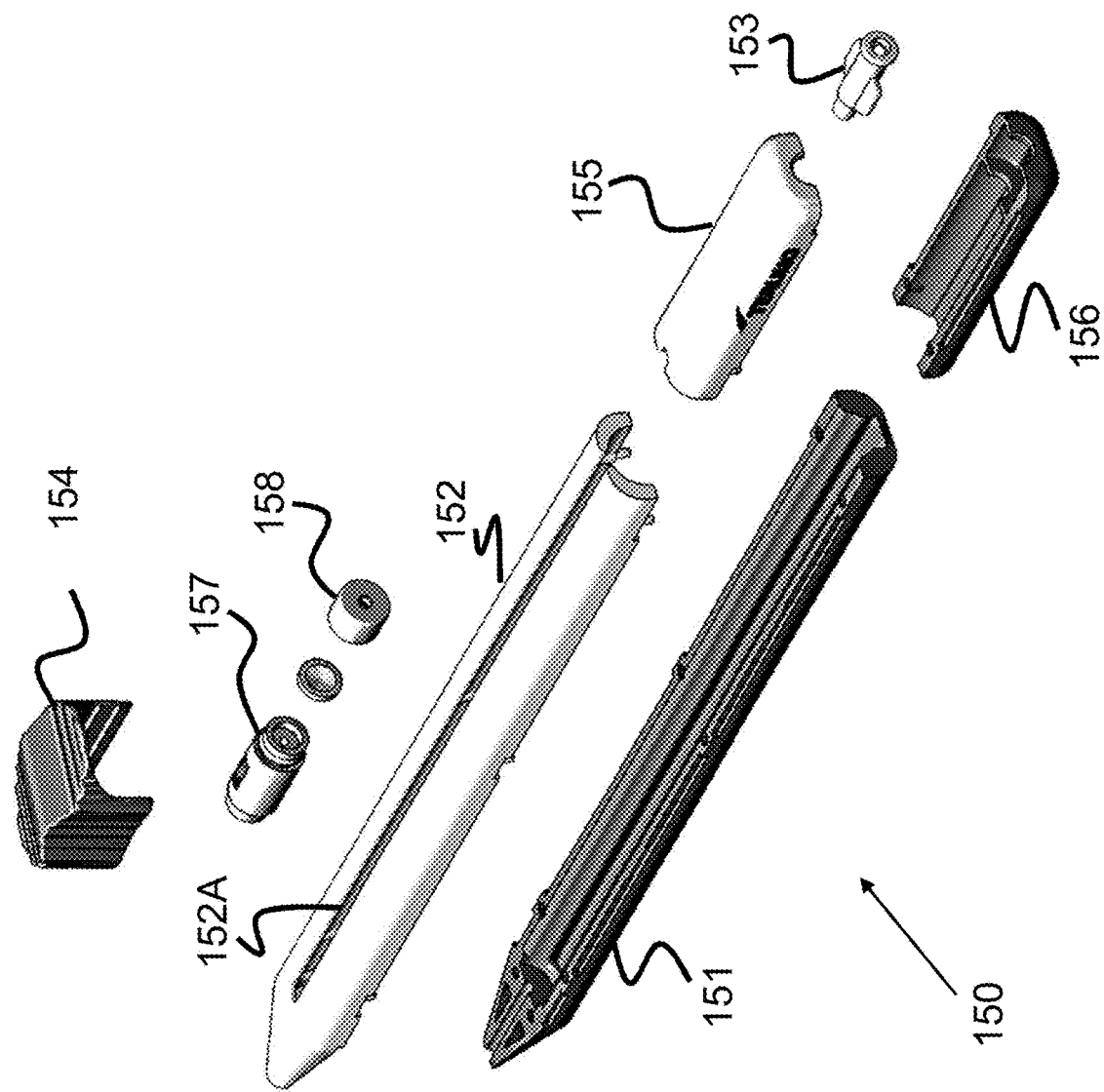
FIG. 15 illustrates an exploded view of a handle assembly with a sliding mechanism according to one embodiment.
Figure 16:
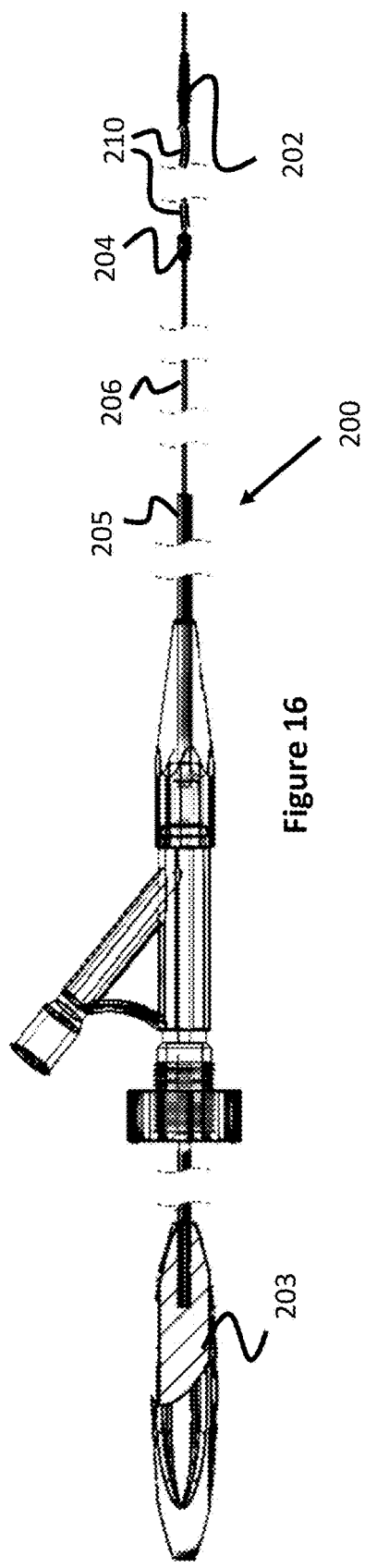
FIG. 16 illustrates a side view of an implant delivery system according to one embodiment.

FIGS. 12-15 illustrate another embodiment of a handle assembly 150. This handle assembly 150 has a sliding element 154 that can be moved by the user along the longitudinal aperture 152A of the housing member 152. In one embodiment, the sliding element 154 is configured to engage the sheath/catheter which overlies the implant and pusher, in order to retract the catheter to expose the implant. The sliding element 154 is connected to a sheath or catheter engagement assembly comprised of a distal element 157 and a proximal element 158 that screws on to the distal element 157, as best shown in FIGS. 14-15. The sheath/catheter 3 may be passed through the aperture of the distal element 157. The proximal element 158 is advanced over the catheter (not shown) and screwed on to the distal element 157, creating a clamping force on the catheter/sheath and thereby engaging the sheath with the sliding element 54. The catheter houses a delivery pusher and implant connected to the pusher, both the internal pusher and the overlying catheter are attached to the proximal end of the handle assembly 150.

The main portion of the handle assembly 150 is comprised of both the upper housing member 152 and lower housing member 151 that engage each other and form a longitudinal cavity. However, the assembly 150 also includes a proximal portion formed between housing members 155 and 156. This separate housing portion allows the top housing member 155 to be opened up so that the proximal hub 153 of the pusher (which is internal of the sheath) can be locked into place and prevented from moving. In this respect, a pusher can be loaded into the handle assembly 150 by the user.

The slider initially is on the distal part of the longitudinal opening 152A and is connected to the sheath as described earlier. The physician pulls the slide proximally to retract the sheath and thereby expose the implant. In one embodiment, the implant is preloaded within a distal portion of the catheter, such that retracting the slider will retract the sheath so that the distally loaded implant will then expand and be delivered. The pusher is lockable in the manner describe above (either through mechanism 153, or by being commonly attached along with the sheath at a proximal end of handle assembly 150). Though pre-loading the implant along a distal portion of the catheter is not required, one advantage is that only a small portion of the catheter would need to be retracted to deploy the implant, meaning the handle length can be fairly small.

Alternative embodiments of the handle of FIGS. 12-15 can utilize the slider instead being connected to a unitary pusher body (rather than the overlying catheter), where the physician would distally move the slider to propel the pusher forward. The slider would initially be placed in a proximal-most configuration along the handle and then moved distally to propel the pusher and implant forward. In one embodiment, the slider moves the pusher and the pusher is preloaded along a distal portion of the overlying catheter—though such a configuration isn't required, one advantage is that the pusher would only have to be moved a small distance to deploy the implant, thereby minimizing the overall length of the handle/implant delivery mechanism. Alternative embodiments can utilize the inner/outer or proximal/distal pusher embodiments described above with regard to the handle assemblies of FIGS. 2-4 and 10-11 with this particular embodiment. Alternative embodiments can further utilize a telescopic functionality, for instance by using the pin configuration of FIG. 1C where the slider element is connected to the pin to advance an inner pusher element forward in a telescopic manner in order to advance an implant.

The handle assemblies and embodiments directed to advancing or retracting portions of a pusher system can be used with a variety of different pusher types and implant types, such as those shown in U.S. Pub. No. 2017/0079820 which is hereby incorporated by reference in its entirety. An implant configured to be attached to a delivery system is shown in U.S. Pub. No. 2017/0042548 which is hereby incorporated by reference in its entirety. Some of these pusher/delivery systems are described in greater detail below. It should be understood that any of the prior-described pusher movement mechanisms can be used to move portions of the pusher systems described further below. Specifically, the outer sleeve/proximal pusher portion or sheath (meaning, whichever portion engages with the handle actuation mechanism) can be moved relative to the inner elements and implants, or the inner elements and implants (meaning, whichever portion engages with the handle actuation mechanism) can be moved relative to the outer sleeve or sheath.

Figure 17:
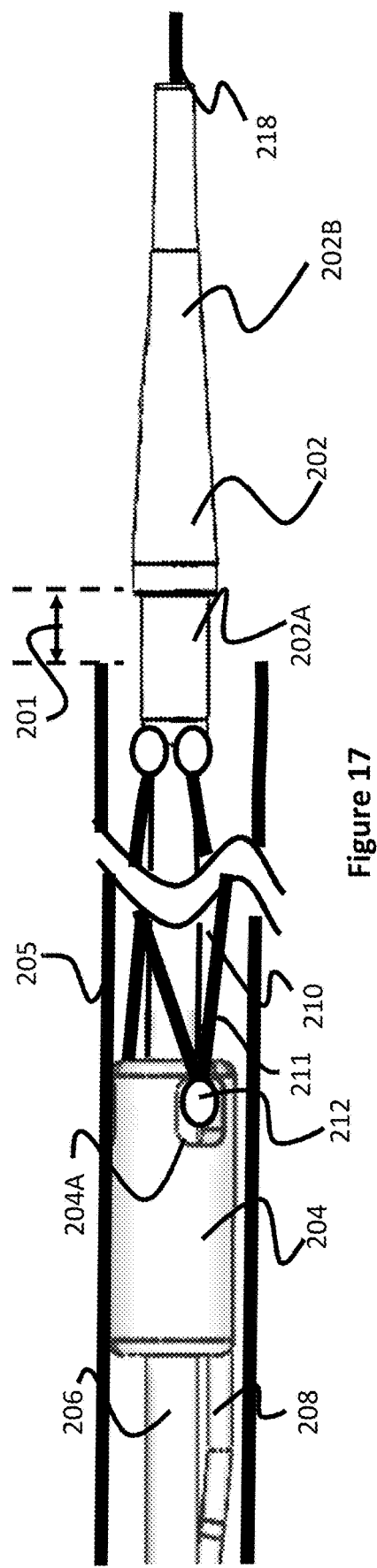
FIG. 17 illustrates a magnified view of a distal end of the implant delivery system of FIG. 16.

The specification up until this point has focused primarily on the pusher systems or mechanical handle to control a pusher or sheath, but not really on the pusher/implant connection to show how the pusher connects to the implant to control its position. The following description is meant to show how the telescoping and handle implant delivery systems can physically link with the actual implant, through a pusher mechanism. FIGS. 16-19 illustrate a delivery system 200 for a vascular implant (e.g., a stent) having a pushing mechanism configured to push the stent 210 out of the end of an outer catheter sleeve or sheath 205. As best seen in FIG. 17, the delivery system 200 includes an elongated tube 206 that extends between the proximal and distal ends of the delivery system 200 within sheath 205; the elongate tube 206 allows passage of a guidewire used to navigate the implant system to a treatment location in the vasculature. The stent 210 is pushed through and out from sheath 205 by a sliding pusher element 204 that has an internal passage through which the elongated tube 206 is disposed. The pusher element 204 can therefore slide axially along a portion of the tube 206 without also moving the tube 206 or sheath 205. In other words, the pusher element 204 is independently movable with respect to both. The pusher element 204 also releasably connects to a proximal end of the stent 210, which allows the pusher element 204 to distally push the stent 210, but also proximally retract the stent 210 prior to its full release and deployment. This pusher element 204 would function as the pusher component of the various handle concepts described earlier and would act as the portion of the pusher which is actually connected to the implant.

Figure 20:
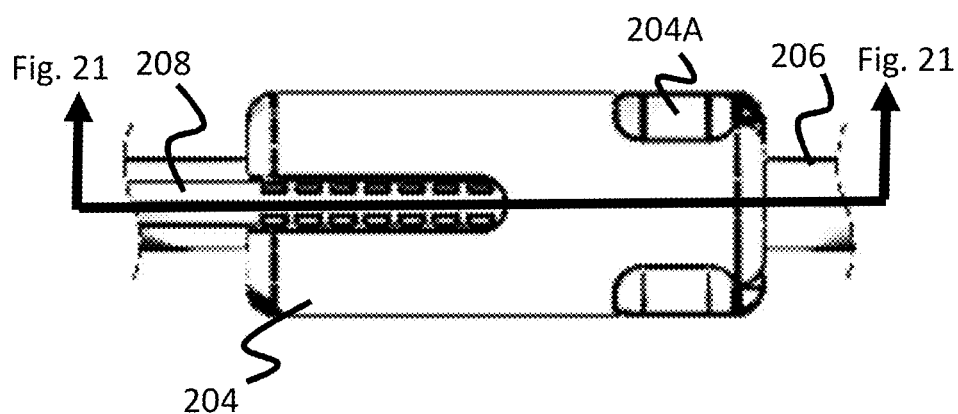
FIG. 20 illustrate a sliding pusher element of the implant delivery system of FIG. 16.
Figure 21:
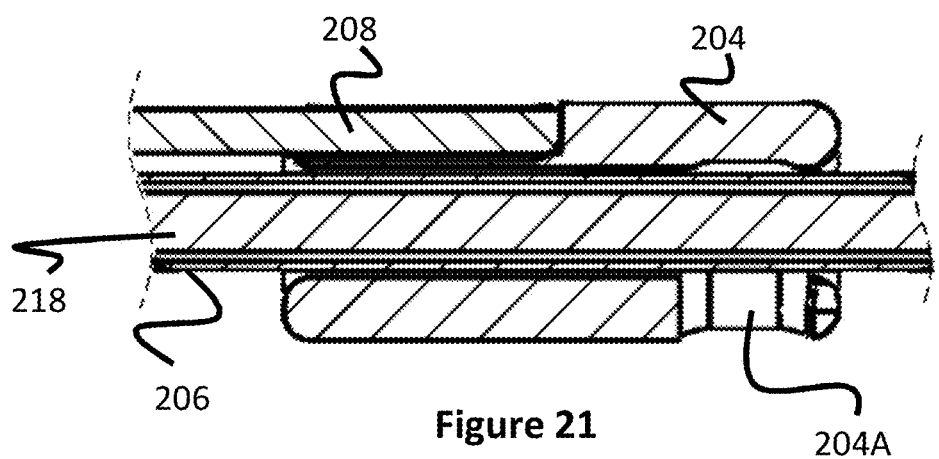
FIG. 21 illustrate a sliding pusher element of the implant delivery system of FIG. 16.
Figure 22:
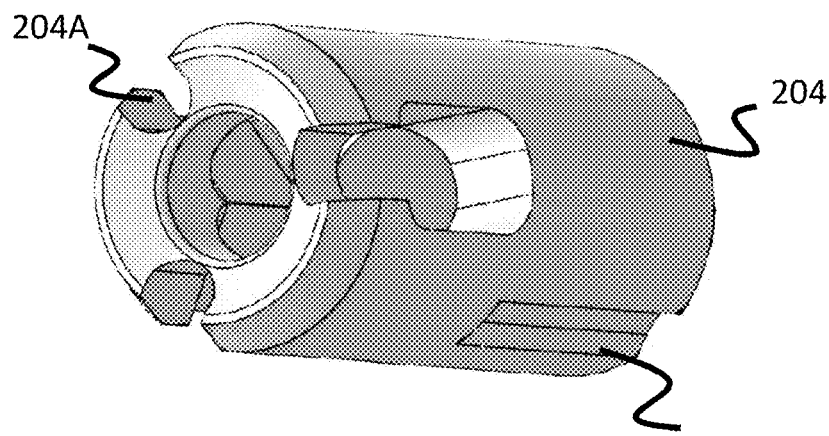
FIG. 22 illustrate a sliding pusher element of the implant delivery system of FIG. 16.
Figure 23:
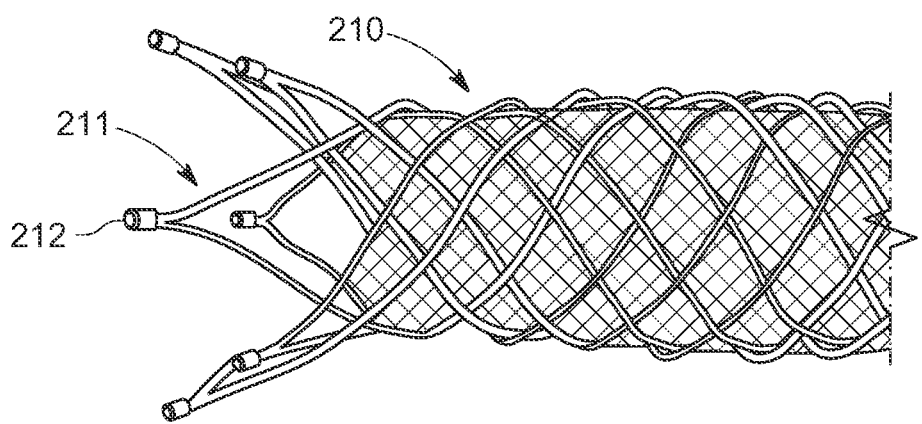
FIG. 23 illustrates an example stent that can be used with the implant delivery system of FIG. 16.

A proximal portion of stent 210 is connected to the pusher element 204 while a distal portion of the stent is connected to distal member 202. Distal member 202 is also slidable over the tubular member 206, meaning the stent 210, pusher element 204, and distal element 202 are all connected and slidable over the tube 206. Referring to FIGS. 20-22, in one embodiment, the stent 210 releasably connects to the pusher element 204 by enlarged bulbs 212 that are fixed on the proximal end of the stent 210 (such as on the proximal ends of stent loops 211) and that fit into apertures or depressions on the outer surface of the pusher element 204. The sheath 205 maintains the bulbs 212 in the depressions 204A, further preventing radial expansion of the stent 210. When the pusher element 204 moves distally beyond the distal end of the outer sheath 205, the proximal end of the stent 210 expands, allowing the bulbs 212 to move out of the depressions 204A and thereby disengage from the pusher element 204. In one embodiment, the depression 204A is somewhat oversized relative to the bulbs 212 size, allowing for some "play" or movement within the depression 204A. Distal member 202 also contains apertures or depressions that accommodate distal bulbs of the stent such that the configuration shown in FIG. 23 represents the proximal and distal end configuration of the stent. In this manner, as the stent is pushed over the elongated tube 206, it is held at its proximal end by the slidable pusher 204 and at its distal end by the enlarged end member 202. The pusher 204 slides the stent over the elongated tube 206, where the stent is held at its proximal end by slidable pusher 204 and at its distal end by slidable distal member 202.

Figure 18:
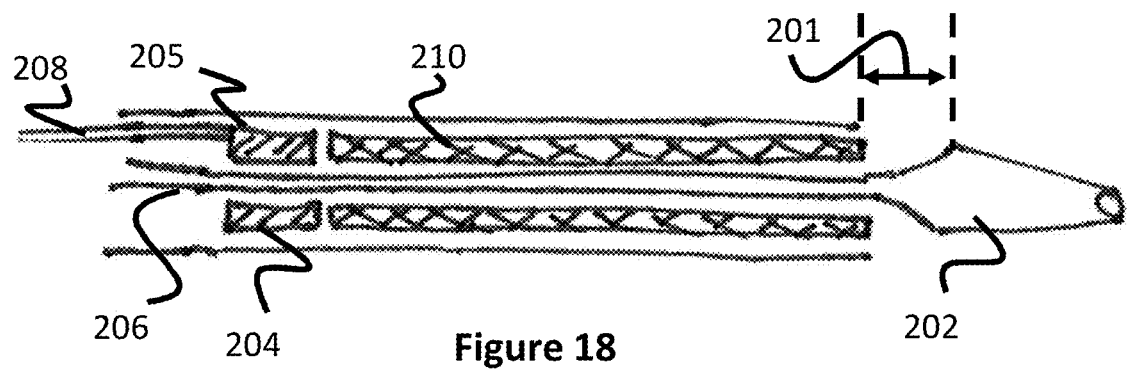
FIG. 18 illustrates a side view of the implant delivery system of FIG. 16 deploying a stent.
Figure 19:
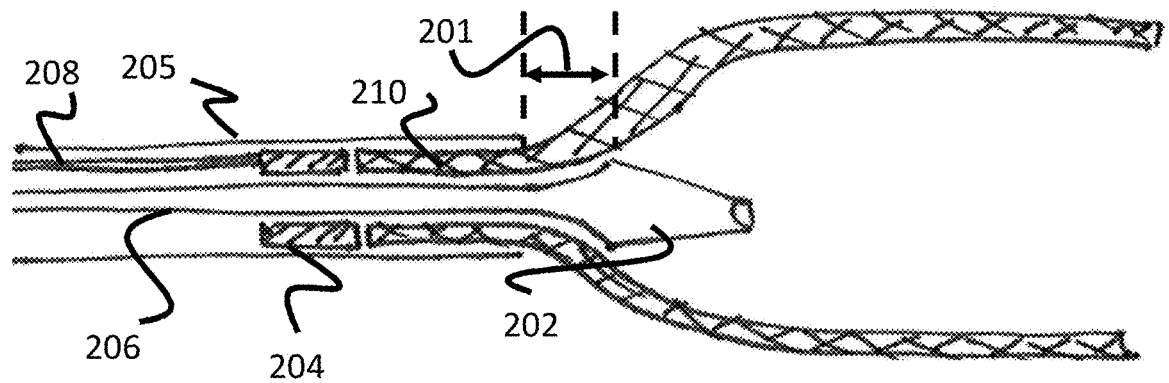
FIG. 19 illustrates a side view of the implant delivery system of FIG. 16 deploying a stent.

The distal end of the elongated tube 206 has an enlargement and the distal member 206 contains a lumen such that it slides over the elongated tube 206; the tube enlargement is larger than this lumen so that the distal member 206 is prevented from falling completely off the tube 206, in other words there is a limit to how far the distal member 206 can slide over the tube. As shown in FIGS. 17-19, when the stent is propelled distally to a point near the distal end of the overlying sheath 205, a small gap 201 is present between the sheath and the distal member 202 and the stent starts expanding out of this gap to expand. At this location, the distal member 202 is prevented from further distal movement due to contacting the enlargement along the underlying elongated tube 206. With the distal member 202 now prevented from further distal movement, the pusher member 204 continues to propel the stent out of the sheath 205 until the stent is fully deployed and expanded; whereby the stent is no longer connected to pusher member 204.

The depression 204A preferably provides only an axial restraint to the bulb 212. If the depression 204A is large enough, the bulb 212 may also have some vertical movement (perpendicular relative to the axis of the device). However, preferably the overall clearance is limited in order to limit the amount of wasted energy involved in pushing and pulling the implant delivery device 200, as well as to limit the amount of jostling the stent 210 undergoes during delivery. Radially, the bulb 212 and stent 210 are restrained by the sheath 205 rather than depression 204A.

The stent 210 can be seen further in FIG. 23 and additional details of the bulbs 212 and its alternatives can be found in U.S. Pub. No. 2017/0079812, which was previously incorporated by reference. In one embodiment, the stent 210 (or stent-graft) is comprised of a mesh of wires. In one embodiment the implant is a stent or stent-graft comprised of a mesh of wires and comprising two layers—an inner layer and an outer layer. The wire meshes end at the proximal and distal ends of the stent leaving open pairs of wire ends. Cap or bulbs 212 may be placed over these open wire ends to secure the open ends and to prevent the open ends from traumatizing the vessel. These caps or bulbs 212 also provide a holding surface for the depressions of the slidable pusher member 204 and distal member 202 which hold the stent as it glides over the elongated tube 206.

The pusher element 204 is axially moved by a connection to a physician-actuated pusher rod 208. The pusher rod 208 is connected to the pusher element 204 and to a handle 203 at the proximal end of the delivery device 200, allowing the physician to move the handle 203 proximally or distally to thereby move the pusher element 204 proximally or distally. In one embodiment, the pusher rod 208 connects to the pusher element 204 at a location that is radially offset from a center of the pusher element 204, allowing the tube 206 to pass through the center of the pusher element 204 (seen in FIGS. 20-22).

The distal member 202 preferably has an elongated, conical region 202B that proximally increases in diameter to reduce trauma as the delivery device 200 is advanced through the patient. The distal end member 202 also includes a reduced diameter region 202A that increases in diameter in the distal direction, which helps radially expand and direct outwards the distal end of the stent 210 as it is distally advanced within the sheath 205. As discussed earlier, the proximal portion of the distal end member 202 may also include depressions (similar to depressions 204A) that help maintain the position of the distal bulbs 212 prior to the commencement of the stent 210 deployment.

The presence of distal member 202 provides a few benefits. First, it provides an atraumatic surface for minimizing blood vessel trauma during tracking within the vasculature, since distal member 202 is preferably made of a soft, polymeric material. Second, distal member 202 provides a ramping surface for the implant (i.e., region 202A). When the stent 210 is expelled from the sheath 205, it will open up relatively quickly since the stent 210 is kept in a restrained state due to the compressive force of the sheath 205. Many implants are made of a shape memory material, so they quickly adopt their expanded configuration when released from a sheath 205. Instead of an abrupt opening, the region 202A provides a ramped, controlled opening as the inner surface of the stent 210 contacts the region 202A while the stent 210 is pushed out. Such a controlled delivery is also beneficial to aid retraction, thereby aiding in positioning and repositioning of the implant prior to complete expansion/deployment.

The proximal region 202A of distal end member 202 preferably has a relatively abrupt transition region as shown in FIG. 17. However, this region 202A can be varied to create a region with a larger or a smaller taper. The remaining portions of the distal end member 202 may have a relatively consistent diametrical profile or may gradually taper to a smaller diameter as shown in FIG. 17. Other variations are possible, including abrupt tapering to a smaller diameter and/or larger diameter region. A gradual taper to a smaller diameter may be desirable to limit the potential contact surface area between distal end member 202 and the blood vessel, while also providing an atraumatic contact surface between the delivery system 200 and the vasculature. Various other shapes are possible for the overall profile of distal end member 202, such as an ovular or balloon-like shape, or a football-like shape.

In FIGS. 18 and 19, the simplified views of the delivery system 200 illustrate the operation for delivering the stent 210. First, a guidewire 218 is placed through tube 206 at or near a desired target location within the vasculature of a patient. Next, the delivery device 200 is tracked over the guidewire 218. Once the distal end of the delivery device 200 is positioned at or near the target location, the physician distally advances the handle 203, thereby distally moving the pusher rod 208, the pusher element 204. Since the stent 210 is also connected to the pusher element 204, translating the pusher element in turns translate the stent 210 and also the distal member 202 which is also distally connected to the stent. As the distal end of the stent 210 moves forward, the tapered or conical portion 202A of the distal end member 202 helps direct the stent 210 out through the gap 201 between the distal end of the sheath 205 and the largest diameter portion of the distal end member 202. As described earlier, the distal member 202 can only move so far with respect to the underlying tube 206 with respect to the distal end of the tube 206, represented by the configurations of FIGS. 18-19 where the distal member 202 has reached its distal most position, creating a gap 201 between the sheath 205 and distal member 202, which the stent 210 emerges from.

Figure 24:
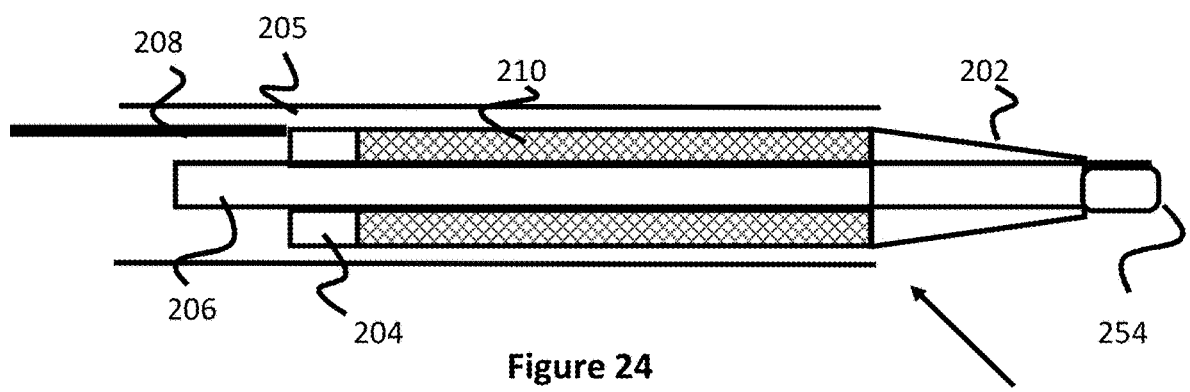
FIGS. 24-27 illustrate the implant delivery system of FIGS. 17-19 in further detail.
Figure 25:
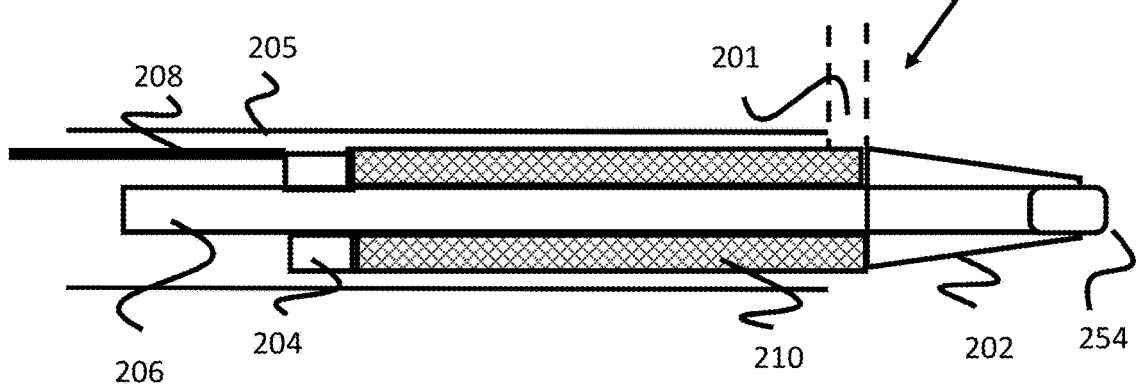

FIGS. 24-27 show further details of the delivery system 200, and focuses more on the enlargement along the elongated tube and its interplay with distal element 202—discussed above. The system 200 includes a distal member 202 that is connected to a distal end of the stent 210 and slides distally during a deployment procedure. In this regard, the system 200 in one embodiment has a stent that is pre-loaded at a distal region of the catheter and that can be delivered with the distal member 202 maintaining the distal end of the sheath 205 in a closed position, as seen in FIG. 24—in this regard distal member functions as a distal tip abutting the sheath in a first configuration, and spaced from the sheath in a second deployed configuration where the stent is released from the sheath 205. As the stent 210 is pushed distally, it pushes the distal member 202 distally, creating the gap 201 between the sheath 205 and the distal member 202 through which the stent 210 is deployed, as seen in FIG. 25.

Figure 27:
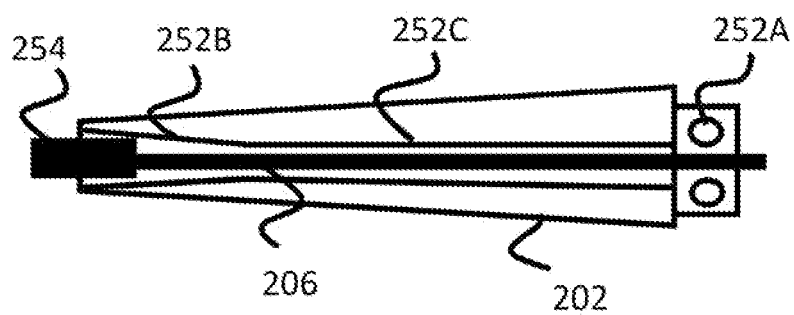

The distal member 202 is prevented from moving off the distal end of the tube 206 by stopper 254, which is fixed to the tube 206—as described above. As best seen in FIG. 27, the distal member 202 has an interior passage having a distal, larger diameter region and a proximal, smaller diameter region. The stopper 254 can pass into the larger diameter region 252B but is too large for the smaller diameter region 252C, thereby preventing the distal member 202 from moving further. The stopper 254 has a generally cylindrical shape, but may alternately have a conical shape that decreases in the proximal direction.

Figure 26:
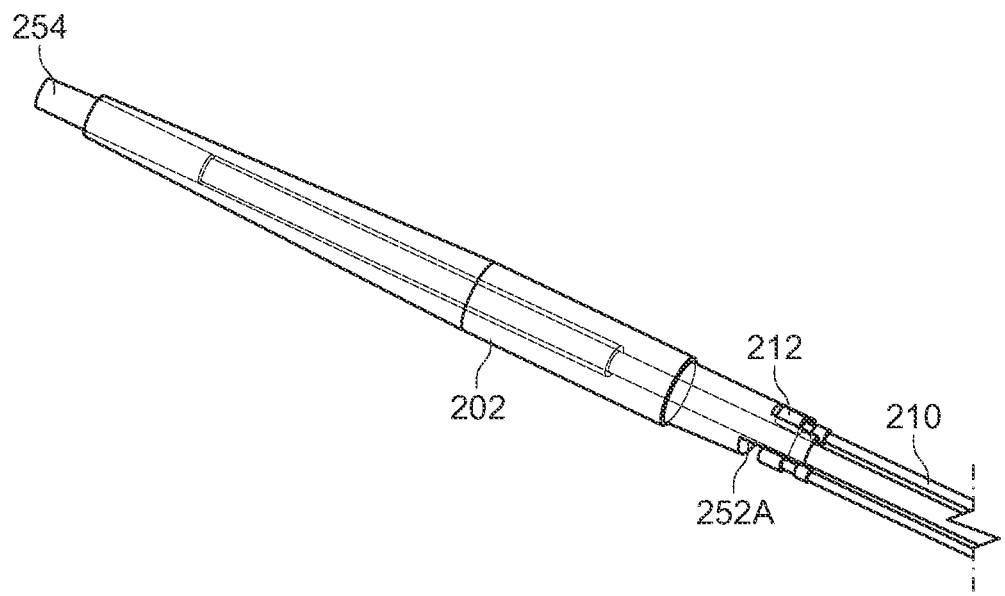

As best seen in FIG. 26, the proximal end of the distal member 202 includes a plurality of depressions or surfaces to help engage the bulbs 212 on the distal end of the stent—as discussed above. As the stent 210 is distally advanced, the bulbs 212 contact and push the distal member 202 until the stopper 254 is reached.

The configuration(s) shown in FIGS. 16-27 are meant to show how an implant would connect to a broader implant and pusher delivery system. In one example, the stent is preloaded in a distal region of the sheath, and the user simply uses the earlier described handle mechanisms to either distally push the pusher 206 or proximally retract the sheath 205 to deploy the stent. In one example, no distal preloading is used, and instead the pusher 206 system is used to push the stent through the overlying sheath 205. In one example, the slidable pusher 206 takes the form of the distal telescoping pusher element connected to the stent implant, shown and described in FIGS. 1A-1C above.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A vessel prosthesis delivery device comprising:
a proximal handle;
an actuator connected to the proximal handle;
a pusher comprising 1) an elongated first member having a series of projections arranged longitudinally on its outer surface; and, 2) an elongated second member extending from the elongated first member and being engaged with a vessel prosthesis at a distal end of the delivery device; wherein the elongated first member and the elongated second member telescope with each other;
a sheath connected to the proximal handle; wherein the elongated first member and the vessel prosthesis are positioned within the sheath; and,
a pin extending between the elongated first member and the elongated second member, wherein the pin is movable to distally translate the elongated second member relative to the elongated first member;
wherein the actuator of the proximal handle engages the projections of the first member to move the first member relative to the proximal handle and the sheath, thereby delivering the vessel prosthesis.

2. The vessel prosthesis delivery device of claim 1, wherein the actuator further comprises a thumb wheel that rotates on an axis perpendicular to a longitudinal axis of the handle; the thumb wheel having a plurality of outer teeth that engage with the series of projections on the outer surface of the elongated first member.

3. The vessel prosthesis delivery device of claim 2, further comprising a removable locking pin that engages and prevents longitudinal movement of the elongated first member.

4. The vessel prosthesis delivery device of claim 2, wherein the proximal handle comprises a track in which the elongated first member is positioned; the track being arranged to allow proximal retraction of the elongated first member without a proximal end of the elongated first member exiting from the proximal handle.

5. The vessel prosthesis delivery device of claim 4, wherein the proximal handle further comprises one or more rollers positioned along the track in the proximal handle so as to change a direction of the elongated first member as it is retracted.

6. The vessel prosthesis delivery device of claim 1, wherein the actuator of the proximal handle engages the projections of the first member to move the first member relative to the proximal handle and the sheath, and thereby moves the vessel prosthesis out of a gap between the sheath and a distal tip located near a distal end of the sheath.

7. The vessel prosthesis delivery device of claim 1, wherein the elongated second member telescopes within the elongated first member.

8. The vessel prosthesis delivery device of claim 1, wherein the pin is located underneath the series of projections.

9. A vessel prosthesis delivery device comprising:
a proximal handle;
a sheath longitudinally fixed to the proximal handle;
a user actuation mechanism connected to the proximal handle;
a pusher comprising 1) an elongated first member positioned within the proximal handle and having a plurality of raised structures regularly repeating along its outer surface; and, 2) an elongated second member extending from a distal end of the elongated first member and connected to a vessel prosthesis; wherein the elongated first member and the vessel prosthesis are positioned within the sheath; wherein the elongated first member and the elongated second member telescope with each other; and,
a pin extending between the elongated first member and the elongated second member, wherein the pin is located underneath the plurality of raised structures;
wherein the user actuation mechanism of the proximal handle contacts the plurality of raised structures of the elongated first member to move the elongated first member relative to the proximal handle and the sheath, thereby delivering the vessel prosthesis.

10. The vessel prosthesis delivery device of claim 9, wherein the user actuation mechanism comprises a thumb wheel that rotates on an axis perpendicular to a longitudinal axis of the proximal handle; the thumb wheel having a plurality of outer teeth that engage with the plurality of raised structures on the outer surface of the elongated first member.

11. The vessel prosthesis delivery device of claim 10, wherein the proximal handle comprises a curved track in which the elongated first member is positioned; the track being arranged to maintain a proximal end of the elongated first member within the handle when proximally retracted.

12. The vessel prosthesis delivery device of claim 9, wherein the user actuation mechanism of the proximal handle contacts the plurality of raised structures of the elongated first member to move the elongated first member relative to the proximal handle and the sheath, and thereby moves the vessel prosthesis out of a gap between the sheath and a distal tip located near a distal end of the sheath.

13. The vessel prosthesis delivery device of claim 9, wherein the pin is movable to distally translate the elongated second member relative to the elongated first member.

14. A vessel prosthesis delivery device comprising:
a proximal handle having an actuation mechanism;
a sheath longitudinally fixed in place relative to the proximal handle;
a vessel prosthesis engagement structure having a proximal member having an outer thread extending along a length of an outer surface of the proximal member, and having a distal member connected to the proximal member and to a vessel prosthesis; wherein the distal member and the vessel prosthesis are positioned within the sheath; wherein the proximal member and the distal member telescope relative to each other; and,
a pin extending between the proximal member and the distal member, and wherein the pin is movable to distally translate the distal member relative to the proximal member;
wherein the actuation mechanism of the proximal handle contacts the outer thread of the proximal member to move the proximal member relative to the handle and the sheath, thereby delivering the vessel prosthesis.

15. The vessel prosthesis delivery device of claim 14, wherein the actuation mechanism comprises a thumb wheel that rotates on an axis perpendicular to a longitudinal axis of the handle; the thumb wheel having a plurality of outer teeth that engage with the outer thread.

16. The vessel prosthesis delivery device of claim 14, wherein the proximal handle includes a locking pin that is removably positioned into the proximal handle to thereby contact the proximal member and prevent longitudinal movement of the proximal member.

17. The vessel prosthesis delivery device of claim 14, the actuation mechanism of the proximal handle contacts the outer thread of the proximal member to move the proximal member relative to the handle and the sheath, and thereby moves the vessel prosthesis out of a gap between the sheath and a distal tip located near a distal end of the sheath.

* * * * *